(12) United States Patent
Phoolchund et al.

(10) Patent No.: US 12,137,994 B2
(45) Date of Patent: Nov. 12, 2024

(54) INTERFACING A SURGICAL ROBOTIC ARM AND INSTRUMENT

(71) Applicant: CMR Surgical Limited, Cambridge (GB)

(72) Inventors: Nikki Priyam Su-Ling Phoolchund, Cambridge (GB); Keith Marshall, Cambridge (GB); Thomas Bates Jackson, Cambridge (GB); Jonathan Peter Whittle, Cambridge (GB); Dominic Martin McBrien, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 2 days.

(21) Appl. No.: 18/055,106

(22) Filed: Nov. 14, 2022

(65) Prior Publication Data

US 2023/0074346 A1 Mar. 9, 2023

Related U.S. Application Data

(63) Continuation of application No. 16/333,081, filed as application No. PCT/GB2017/052709 on Sep. 14, 2017, now Pat. No. 11,547,501.

(30) Foreign Application Priority Data

Sep. 14, 2016 (GB) .................................... 1615616
Jun. 6, 2017 (GB) .................................... 1709016

(51) Int. Cl.
*A61B 17/072* (2006.01)
*A61B 34/30* (2016.01)
(Continued)

(52) U.S. Cl.
CPC ............ *A61B 34/30* (2016.02); *A61B 17/072* (2013.01); *A61B 46/10* (2016.02);
(Continued)

(58) Field of Classification Search
CPC ................ A61B 17/068; A61B 17/072; A61B 17/07207; A61B 17/00234;
(Continued)

(56) References Cited

U.S. PATENT DOCUMENTS 5,820,623 A * 10/1998 Ng .......................... A61B 34/70
606/1
7,666,191 B2 * 2/2010 Orban, III .............. A61B 46/10
606/1

(Continued)

FOREIGN PATENT DOCUMENTS

CN 102018573 4/2011
CN 102551815 7/2012
(Continued)

OTHER PUBLICATIONS

Examination Report issued in Great Britain Patent Application No. GB2202571.2, issued Mar. 22, 2022, 7 pages.
(Continued)

*Primary Examiner* — Scott A Smith
(74) *Attorney, Agent, or Firm* — King & Spalding

(57) ABSTRACT

An interface structure for detachably interfacing a surgical robot arm to a surgical instrument, the interface structure comprising: a base portion comprising a first surface for facing the surgical instrument and a second surface for facing the surgical robot arm; and a plurality of first fasteners supported by the base portion and protruding from the first surface, the plurality of first fasteners configured to engage the surgical instrument so as to retain the interface structure to the surgical instrument. The interface structure (Continued)

engages the surgical robot arm so as to retain the interface structure to the surgical robot arm, wherein the plurality of first fasteners and the remainder of the interface structure are shaped such that when the surgical instrument is detached from the surgical robot arm the interface structure is retained to the surgical robot arm.

7 Claims, 14 Drawing Sheets

(51) Int. Cl.
| | | |
|---|---|---|
| A61B 46/10 | (2016.01) | |
| A61B 17/00 | (2006.01) | |
| A61B 17/068 | (2006.01) | |
| A61B 17/29 | (2006.01) | |
| A61B 17/32 | (2006.01) | |
| A61B 34/00 | (2016.01) | |

(52) U.S. Cl.
CPC .............. *A61B 2017/00393* (2013.01); *A61B 2017/00477* (2013.01); *A61B 17/068* (2013.01); *A61B 17/07207* (2013.01); *A61B 2017/07214* (2013.01); *A61B 17/29* (2013.01); *A61B 2017/2923* (2013.01); *A61B 17/32* (2013.01); *A61B 2034/302* (2016.02); *A61B 34/74* (2016.02); *A61B 34/76* (2016.02)

(58) Field of Classification Search
CPC .............. A61B 17/2909; A61B 17/32; A61B 2017/00017; A61B 2017/00398; A61B 2017/00477; A61B 2017/07214; A61B 2017/2923; A61B 2017/2927; A61B 34/30; A61B 34/32; A61B 34/35; A61B 34/37; A61B 34/70; A61B 34/74; A61B 34/76; A61B 90/08; A61B 90/10; A61B 90/17; A61B 90/30; A61B 90/98; A61B 90/361; A61B 10/0275; A61B 10/0041; A61B 10/0266; A61B 10/0096
USPC .......... 227/19, 175.1, 176.1; 606/1, 41, 130, 606/139, 219; 600/439, 567, 568
See application file for complete search history.

(56) References Cited

U.S. PATENT DOCUMENTS

| | | | | |
|---|---|---|---|---|
| 7,699,855 | B2* | 4/2010 | Anderson | A61B 34/30 606/1 |
| 7,955,322 | B2* | 6/2011 | Devengenzo | B25J 9/1045 606/1 |
| 8,979,871 | B2* | 3/2015 | Tyc | A61B 18/02 606/130 |
| 9,211,160 | B2 | 12/2015 | Pivotto | |
| 9,326,825 | B2* | 5/2016 | Cleary | A61M 5/46 |
| 9,498,291 | B2 | 11/2016 | Balaji | |
| 9,538,991 | B2* | 1/2017 | Menon | A61B 10/0233 |
| 9,687,312 | B2 | 6/2017 | Dachs, II | |
| 9,724,493 | B2 | 8/2017 | Pacheco | |
| 10,512,511 | B2 | 12/2019 | Anvari | |
| 2002/0087049 | A1 | 7/2002 | Brock et al. | |
| 2002/0156395 | A1* | 10/2002 | Stephens | A61B 10/0275 600/568 |
| 2004/0049205 | A1 | 3/2004 | Lee et al. | |
| 2005/0165328 | A1* | 7/2005 | Heske | A61B 10/0275 600/568 |
| 2006/0074344 | A1* | 4/2006 | Hibner | A61B 10/0275 600/568 |
| 2007/0119274 | A1* | 5/2007 | Devengenzo | A61B 34/30 74/490.01 |
| 2007/0239067 | A1* | 10/2007 | Hibner | A61B 10/0041 600/567 |
| 2008/0140088 | A1 | 6/2008 | Orban, III | |
| 2010/0036245 | A1* | 2/2010 | Yu | A61N 5/1027 600/7 |
| 2010/0170519 | A1 | 7/2010 | Romo et al. | |
| 2012/0310112 | A1* | 12/2012 | Fichtinger | A61B 17/3478 600/567 |
| 2013/0218005 | A1* | 8/2013 | Desai | A61B 6/032 600/424 |
| 2013/0296883 | A1* | 11/2013 | Anvari | A61B 10/0266 606/130 |
| 2013/0317519 | A1 | 11/2013 | Romo et al. | |
| 2014/0107665 | A1* | 4/2014 | Shellenberger | A61B 34/37 606/130 |
| 2014/0257333 | A1 | 9/2014 | Blumenkranz | |
| 2014/0263537 | A1 | 9/2014 | Leimbach et al. | |
| 2014/0309661 | A1* | 10/2014 | Sheps | A61M 25/0136 606/130 |
| 2014/0358162 | A1 | 12/2014 | Valdastri et al. | |
| 2015/0119638 | A1* | 4/2015 | Yu | A61B 90/30 600/102 |
| 2015/0257841 | A1 | 9/2015 | Dachs, II | |
| 2016/0058513 | A1 | 3/2016 | Giorgi | |
| 2016/0151115 | A1 | 6/2016 | Karguth et al. | |
| 2017/0086932 | A1* | 3/2017 | Auld | A61B 34/30 |

FOREIGN PATENT DOCUMENTS

| | | |
|---|---|---|
| CN | 205514900 | 8/2016 |
| EP | 3025667 | 6/2016 |
| EP | 3305235 | 4/2018 |
| EP | 3673856 | 7/2020 |
| GB | 2546392 | 7/2017 |
| GB | 2597385 | 1/2022 |
| JP | 2007167643 | 7/2007 |
| JP | 2009525097 | 7/2009 |
| JP | 2016120277 | 7/2016 |
| WO | WO 2009061915 | 5/2009 |
| WO | WO 2012/158449 | 11/2012 |
| WO | WO 2016090459 | 6/2016 |
| WO | WO 2016/178027 | 11/2016 |

OTHER PUBLICATIONS

Great Britain Examination Report issued in application No. GB1801210.4, Jun. 22, 2021, 4 pages.
Great Britain Examination Report issued in application No. GB1709016.8, Jun. 22, 2021, 9 pages.
Examination Report issued in Great Britain Patent Application No. GB1709016.8, issued Jan. 19, 2022, 4 pages.
Office Action issued in Chinese Patent Application No. 201780056182.6, issued Nov. 30, 2021, 19 pages total including translation.
V. Ekstrand, International Search Report issued in application No. PCT/GB2017/052709 com-pletion date Nov. 10, 2017, mailing date Jan. 1, 2018, 6 pages.
International Search Report issued for International Patent Application No. GB1615616.8 on Feb. 23, 2017, 4 pages.
Notice of Reason(s) for Refusal issued in Japanese Patent Application No. 2019-535990, issued Aug. 3, 2021, 13 pages total including translation.
Examination Report for European Patent Application No. 17771538.0, issued Mar. 10, 2023.

* cited by examiner

INTERFACING A SURGICAL ROBOTIC ARM AND INSTRUMENT

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

A surgeon utilises many instruments during the course of a typical laparoscopy operation. For this reason, it is desirable for the instruments to be detachable from and attachable to the end of the robot arm with an ease and speed which enables instruments to be exchanged mid-operation. It is therefore desirable to minimise the time taken and maximise the ease with which one instrument is detached from a robot arm and a different instrument is attached.

The operating theatre is a sterile environment. The surgical robotic system must be sterile to the extent it is exposed to the patient. Surgical instruments are sterilised prior to use in an operation, however the robot arm is not sterilised prior to use. Instead, a sterile drape is placed over the whole of the surgical robot prior to the operation. In this way, the patient is not exposed to the non-sterile surgical robot arm. When exchanging instruments mid-operation, it is desirable for the sterile barrier to be maintained.

SUMMARY OF THE INVENTION

According to an aspect of the invention, there is provided an interface structure for detachably interfacing a surgical robot arm to a surgical instrument, the interface structure comprising: a base portion comprising a first surface for facing the surgical instrument and a second surface for facing the surgical robot arm; and a plurality of first fasteners supported by the base portion and protruding from the first surface, the plurality of first fasteners configured to engage the surgical instrument so as to retain the interface structure to the surgical instrument; the interface structure further configured to engage the surgical robot arm so as to retain the interface structure to the surgical robot arm, wherein the plurality of first fasteners and the remainder of the interface structure are shaped such that when the surgical instrument is detached from the surgical robot arm the interface structure is retained to the surgical robot arm.

Each of the first fasteners may comprise a body and a protrusion from the body, the protrusion configured to engage a nib of the surgical instrument. The protrusion may be parallel to the plane of the base portion. The protrusion may comprise a pair of protruding elements, the pair of protruding elements being shaped so as to in combination retain the nib of the surgical instrument.

The plurality of first fasteners may be shaped so as to when the surgical instrument is attached to the interface structure, restrain the surgical instrument from moving relative to the interface structure in directions perpendicular to the axial direction of the surgical robot arm. The plurality of first fasteners may be shaped so as to when the surgical instrument is attached to the surgical robot arm, restrain the surgical instrument from moving relative to the surgical robot arm in an axial direction of the surgical robot arm.

When the interface structure is attached to the surgical robot arm, the base portion may be parallel to the axial direction of the surgical robot arm.

The base portion may comprise a rim having the first surface and the second surface, the rim surrounding a hollow interior.

The interface structure may further comprise alignment features on the first surface for aiding alignment of the surgical instrument and the surgical robot arm during engagement. The alignment features may comprise studs or recesses.

The interface structure may further comprise a rear wing portion attached to a rear edge of the rim of the base portion, the rear wing portion configured to cover a proximal exposed surface of the surgical robot arm. The rear wing portion may be angled relative to the base portion away from the distal end of the surgical robot arm. The rear wing portion and the base portion may be integrally formed. The rear wing portion may be pivotally connected to the base portion about the rear edge of the rim of the base portion. The rear wing portion may comprise one or more third fasteners for fastening to the proximal exposed surface of the surgical robot arm.

The interface structure may further comprise a front wing portion attached to a front edge of the rim of the base portion, the front wing portion configured to cover a distal exposed surface of the surgical robot arm. The front wing portion and the base portion may be integrally formed. The front wing portion may be pivotally connected to the base portion about the front edge of the rim of the base portion. The front wing portion may comprise one or more fourth fasteners for fastening to the distal exposed surface of the surgical robot arm. Each fourth fastener may comprise a body and a protrusion from the body, the protrusion configured to be retained in a recess in the surgical robot arm. The interior surface of the front wing portion may comprise biasing material for, when the interface structure is engaged on the surgical robot arm, biasing the interface structure against the surgical robot arm.

The interface structure may further comprise an envelope portion which connects opposing edges of the base portion so as to, when engaged on the surgical robot arm, retain the interface structure to the surgical robot arm, wherein the plurality of first fasteners and the envelope portion are shaped such that when the surgical instrument is detached from the surgical robot arm the interface structure is retained to the surgical robot arm. The envelope portion may be shaped so as to, when the interface structure is engaged on the surgical robot arm, circumscribe the exterior surface of the surgical robot arm. The base portion and the envelope portion may be integrally formed. The interior surface of the envelope portion may have a ribbed profile.

The interface structure may further comprise a plurality of second fasteners protruding in an opposing direction to the first fasteners, the plurality of second fasteners configured to engage the surgical robot arm so as to retain the interface structure to the surgical robot arm, wherein the plurality of first fasteners and the plurality of second fasteners are shaped such that when the surgical instrument is detached from the surgical robot arm the interface structure is retained to the surgical robot arm. Each of the second fasteners may comprise a protrusion configured to be retained in a recess in the surgical robot arm.

For each of the first and second fasteners, the protrusion may be angled relative to the body, the protrusions of the second fasteners being more acutely angled than the protrusions of the first fasteners. Each of the first fasteners may be integrally formed with one of the second fasteners. Each of the first fasteners may be integrally formed with one of the second fasteners and the base portion.

When the surgical instrument is attached to the surgical robot arm, the rim may be encompassed within a boundary formed by the external surface of the surgical robot arm in an axial direction of the surgical robot arm, and wherein each second fastener is engageable with a recess in the external surface of the surgical robot arm.

Each fourth fastener may be perpendicular to the first and second fasteners.

The interface structure may further comprise side flange portions, each side flange portion attached to a side edge of the rim of the base portion. Each second fastener may be integrally formed with a side flange portion.

An outer boundary of the interface structure may terminate in a drape. The drape and the interface structure may be integrally formed.

An inner boundary of the interface structure may terminate in a membrane which extends over the hollow interior.

The interface structure may further comprise a wireless receiver for receiving wireless transmissions from the surgical instrument. The wireless receiver may be located on a surgical robot arm facing surface of the interface structure.

According to a second aspect of the invention, there is provided a surgical instrument for use in robotic surgery, the surgical instrument comprising: a shaft; a surgical end effector at a distal end of the shaft; and an interfacing portion at a proximal end of the shaft for interfacing a surgical robot arm via an interface structure, the interfacing portion comprising: a body configured to engage a first fastener of the interface structure; and an engagement portion, the engagement portion displaceable relative to the body transverse to an axial direction of the shaft, wherein the engagement portion is biased towards adopting a position at the end of its displaceable range most distal from the shaft.

The engagement portion may comprise a plurality of nibs, each nib configured to engage with a first fastener of the interface structure when the engagement portion adopts the position at the end of its displaceable range most distal from the shaft. The engagement portion may be configured to disengage with each of the first fasteners of the interface structure when the engagement portion adopts a position at the end of its displaceable range most proximal to the shaft.

The engagement portion may be spring loaded so as to bias its position towards the end of its displaceable range most distal from the shaft.

The engagement portion may comprise a first recess and the body may comprise a second recess, the first and second recesses being co-axial and transverse to the axial direction of the shaft, the surgical instrument further comprising a pin housed partially in the first recess and partially in the second recess, so as to constrain motion of the engagement portion relative to the body transverse to the axial direction of the shaft.

The surgical instrument may further comprise a wireless transmitter for sending wireless transmissions to the interface structure.

According to a third aspect of the invention, there is provided a surgical robot arm for use in robotic surgery, the surgical robot arm comprising: a base; and a series of articulations connecting the base to an interfacing portion at the distal end of the surgical robot arm, the series of articulations enabling the interfacing portion to be articulated relative to the base; the interfacing portion configured to interface a surgical instrument by retaining the interface structure.

BRIEF DESCRIPTION OF THE FIGURES

The present invention will now be described by way of example with reference to the accompanying drawings. In the drawings.

DETAILED DESCRIPTION

Figure 3:
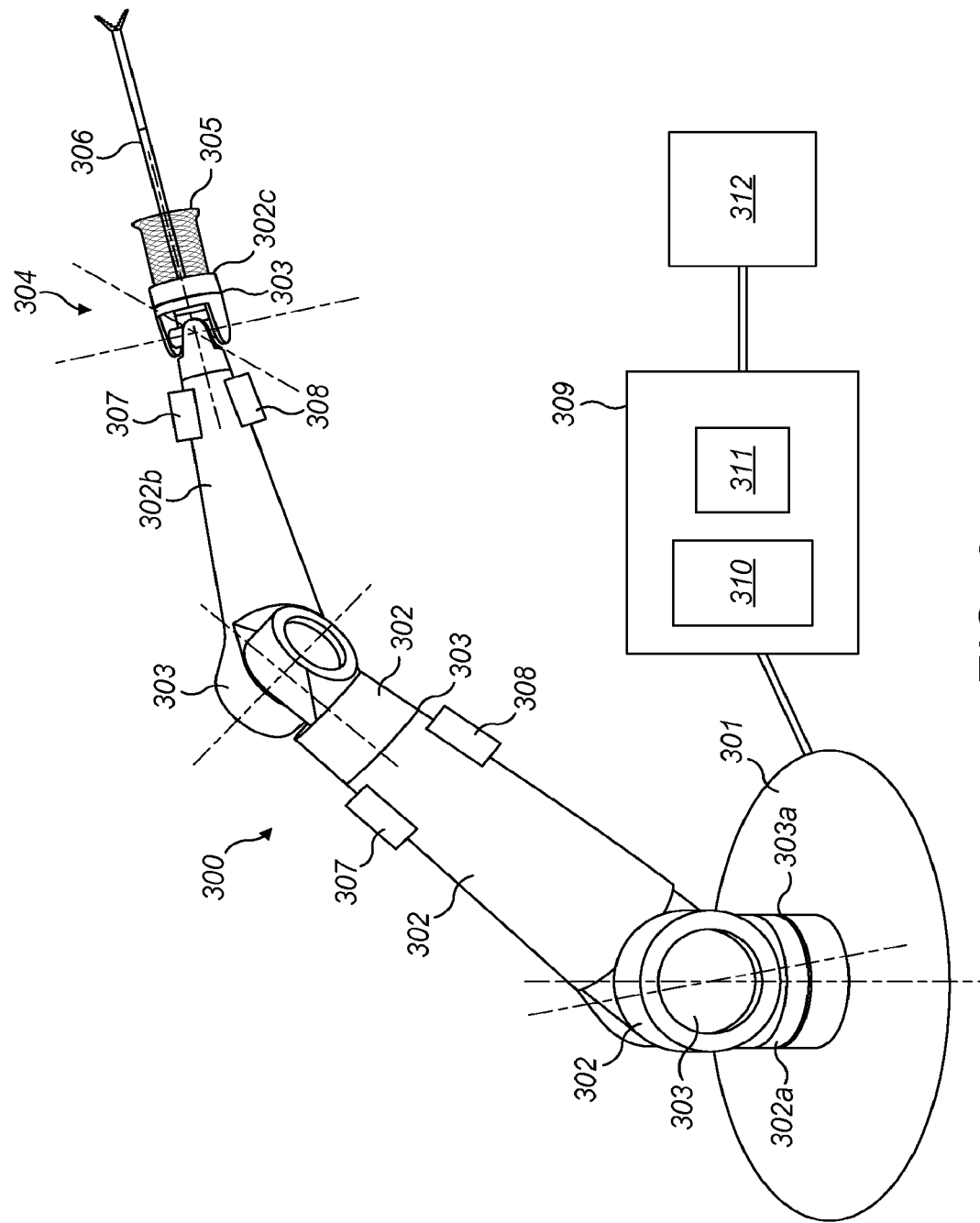
FIG. 3 illustrates a surgical robot.

FIG. 3 illustrates a surgical robot having an arm 300 which extends from a base 301. The arm comprises a number of rigid limbs 302. The limbs are coupled by revolute joints 303. The most proximal limb 302a is coupled to the base by joint 303a. It and the other limbs are coupled in series by further ones of the joints 303. Suitably, a wrist 304 is made up of four individual revolute joints. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

Figure 1:
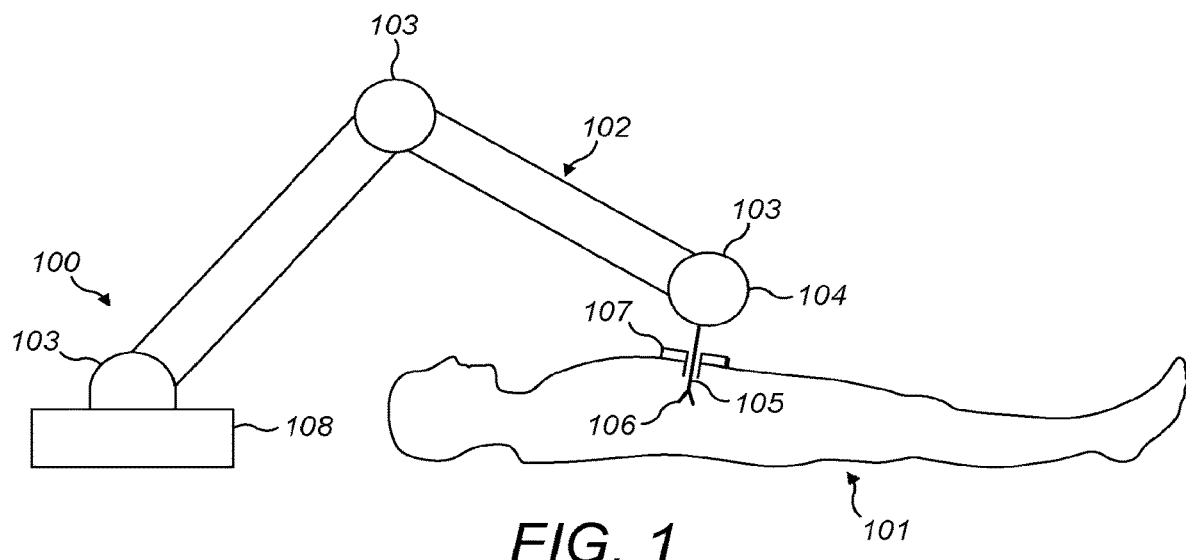
FIG. 1 illustrates a surgical robot performing a surgical procedure.
Figure 2:
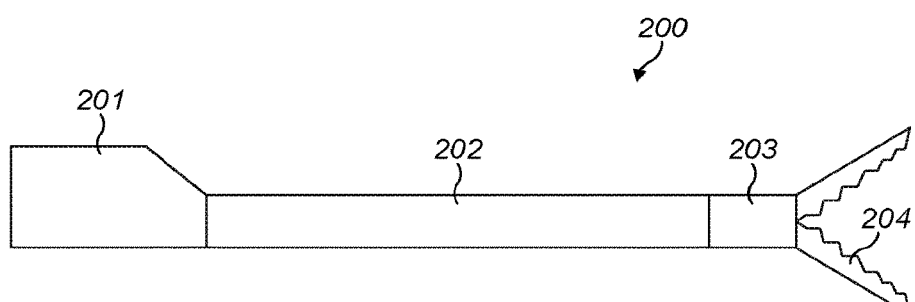
FIG. 2 illustrates a known surgical instrument.

The arm terminates in an attachment 305 for interfacing with the instrument 306. Suitably, the instrument 306 takes the form described with respect to FIG. 2. The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation.

Suitably, the diameter of the profile of the articulation matches or is narrower than the diameter of the shaft. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 309. A control unit 309 comprises a processor 310 and a memory 311. Memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in memory 311 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
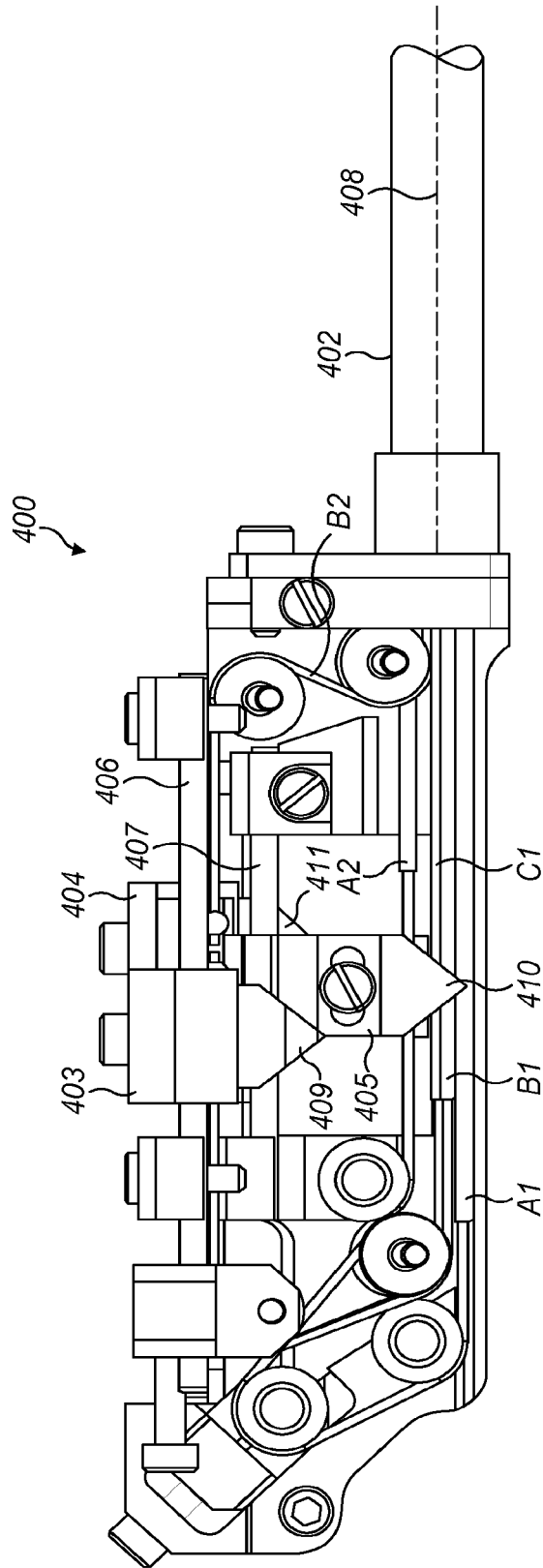
FIG. 4 illustrates an instrument interface.
Figure 5:
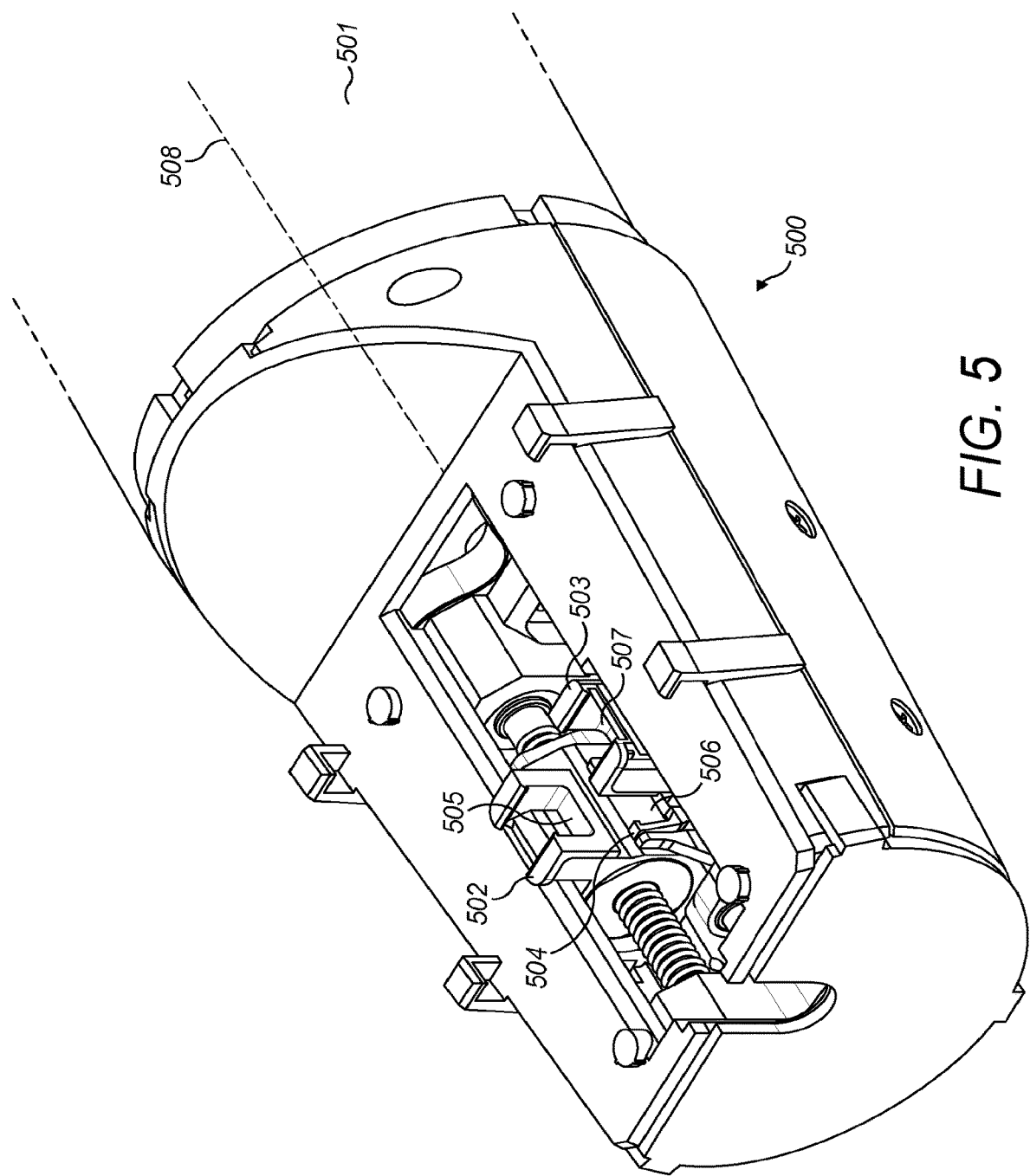
FIG. 5 illustrates a drive assembly interface of a robot arm with attached interface structure.

FIGS. 4 and 5 illustrate an exemplary mechanical interconnection of the drive assembly interface and the instrument interface in order to transfer drive from the robot arm to the instrument. The shaft 402 of the instrument terminates in the instrument interface 400. The instrument interface 400 comprises a plurality of instrument interface elements 403, 404, 405. Pairs of driving elements (A1, A2), (B1, B2), (C1, C2) extend into the instrument interface 400 from the end of the shaft 402. Each pair of driving elements terminates in one of the instrument interface elements. In the example shown in FIG. 4: driving element pair A1, A2 terminates in instrument interface element 405; driving element pair B1, B2 terminates in instrument interface element 403; and driving element pair C1, C2 terminates in instrument interface element 404.

FIG. 4 illustrates three instrument interface elements and three driving element pairs. In other examples, there may be greater than or fewer than three instrument interface elements. There may be greater than or fewer than three driving element pairs. In FIG. 4 there is a one-to-one relationship between instrument interface elements and driving element pairs. In other examples, there may be any other coupling relationship between the instrument interface elements and driving element pairs. For example, a single instrument interface element may drive more than one pair of driving elements. In another example, more than one instrument interface element may drive a single pair of driving elements.

The instrument interface elements are displaceable within the instrument interface. In the example shown, the instrument interface elements are slideable along rails. Instrument interface element 403 is slideable along rail 406 and instrument interface element 405 is slideable along rail 407. Instrument interface element 404 is slideable along a rail (not shown). Each instrument interface element is displaceable along a direction parallel to the direction of elongation of the pair of driving elements which that instrument interface element holds captive. Each instrument interface element is displaceable in a direction parallel to the longitudinal axis 408 of the instrument shaft 402. When the instrument interface element moves along its rail, it causes a corresponding movement to the driving element pair secured to it. Thus, moving an instrument interface element drives motion of a driving element pair and hence motion of a joint of the instrument.

In the example of FIG. 4, each instrument interface element comprises a fin 409, 410, 411 which is the portion of the instrument interface element which engages the drive assembly interface element.

In another example, each drive assembly interface element comprises a fin, and each instrument interface element comprises a socket for receiving the fin of the corresponding drive assembly interface element.

FIG. 5 illustrates an exemplary drive assembly interface 500 at the end of a robot arm 501. Drive assembly interface 500 mates with instrument interface 400. Drive assembly interface 500 comprises structure for receiving the instrument interface elements of the instrument interface of FIG.

4. Specifically, drive assembly interface elements 502, 503, 504 receive instrument interface elements 403, 404, 405. In the example shown, each drive assembly interface element comprises a socket for receiving the fin of the corresponding instrument interface element. Socket 505 of drive assembly interface element 502 receives fin 409 of instrument interface element 403. Socket 506 of drive assembly interface element 504 receives fin 410 of instrument interface element 405. Socket 507 of drive assembly interface element 503 receives fin 411 of instrument interface element 404.

FIG. 5 illustrates three drive assembly interface elements. In other examples, there may be greater than or fewer than three drive assembly interface elements. In FIGS. 4 and 5 there is a one-to-one relationship between instrument interface elements and drive assembly interface elements. In other examples, there may be any other coupling relationship between the instrument interface elements and drive assembly interface elements. For example, a single drive assembly interface element may drive more than one instrument interface elements. In another example, more than one drive assembly interface elements may drive a single instrument interface element.

Each drive assembly interface element is displaceable within the drive assembly. This displacement is driven. For example, the displacement may be driven by a motor and lead screw arrangement. In the example shown, the drive assembly interface elements are slideable along rails. Each drive assembly interface element is displaceable along a direction parallel to the longitudinal axis 508 of the terminal link of the robot arm. When the drive assembly interface element moves along its rail, it causes a corresponding movement to the instrument interface element that it holds captive. Thus, driving motion of a drive assembly interface element drives motion of an instrument interface element which drives articulation of the end effector of the instrument.

Figure 6:
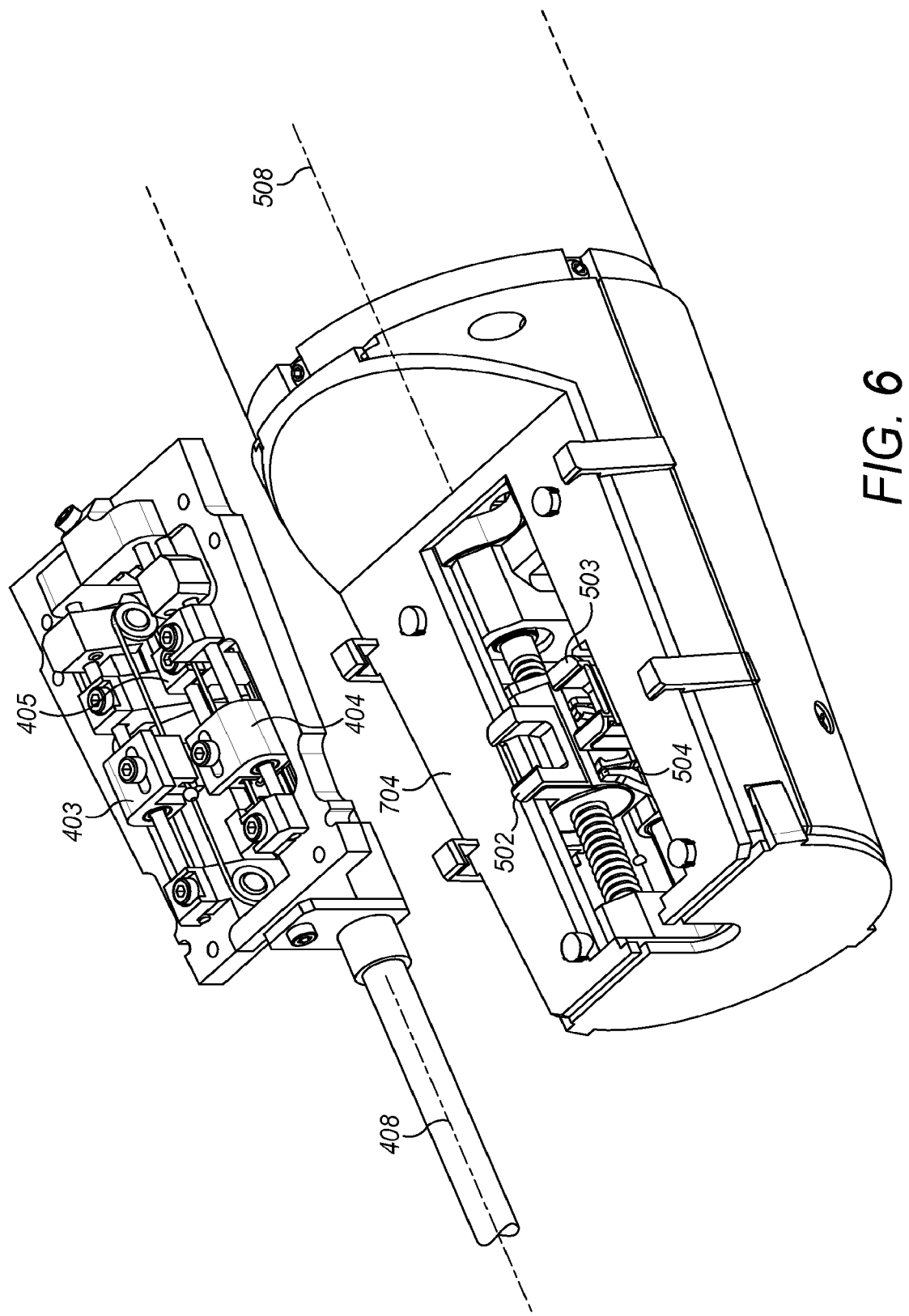
FIG. 6 illustrates an instrument being positioned into engagement with a robot arm.

FIG. 6 illustrates the instrument being placed into engagement with the robot arm. When instrument interface element 403 and drive assembly interface element 502 are engaged, instrument interface element 404 and drive assembly interface element 503 are engaged, and instrument interface element 405 and drive assembly interface element 504 are engaged, the instrument interface elements and the drive assembly interface elements are all displaceable in the same direction. This direction is parallel to both the longitudinal axis of the terminal link of the robot arm 508 and the longitudinal axis of the instrument shaft 408.

During an operation, the surgical robot is shrouded in a sterile drape to provide a sterile barrier between the non-sterile surgical robot and the sterile operating environment. The surgical instrument is sterilised before being attached to the surgical robot. The sterile drape is typically constructed of a plastic sheet, for example made of polyester, polypropylene, polyethylene or polytetrafluoroethylene (PTFE). Suitably, the drape is flexible and/or deformable.

Figure 7:
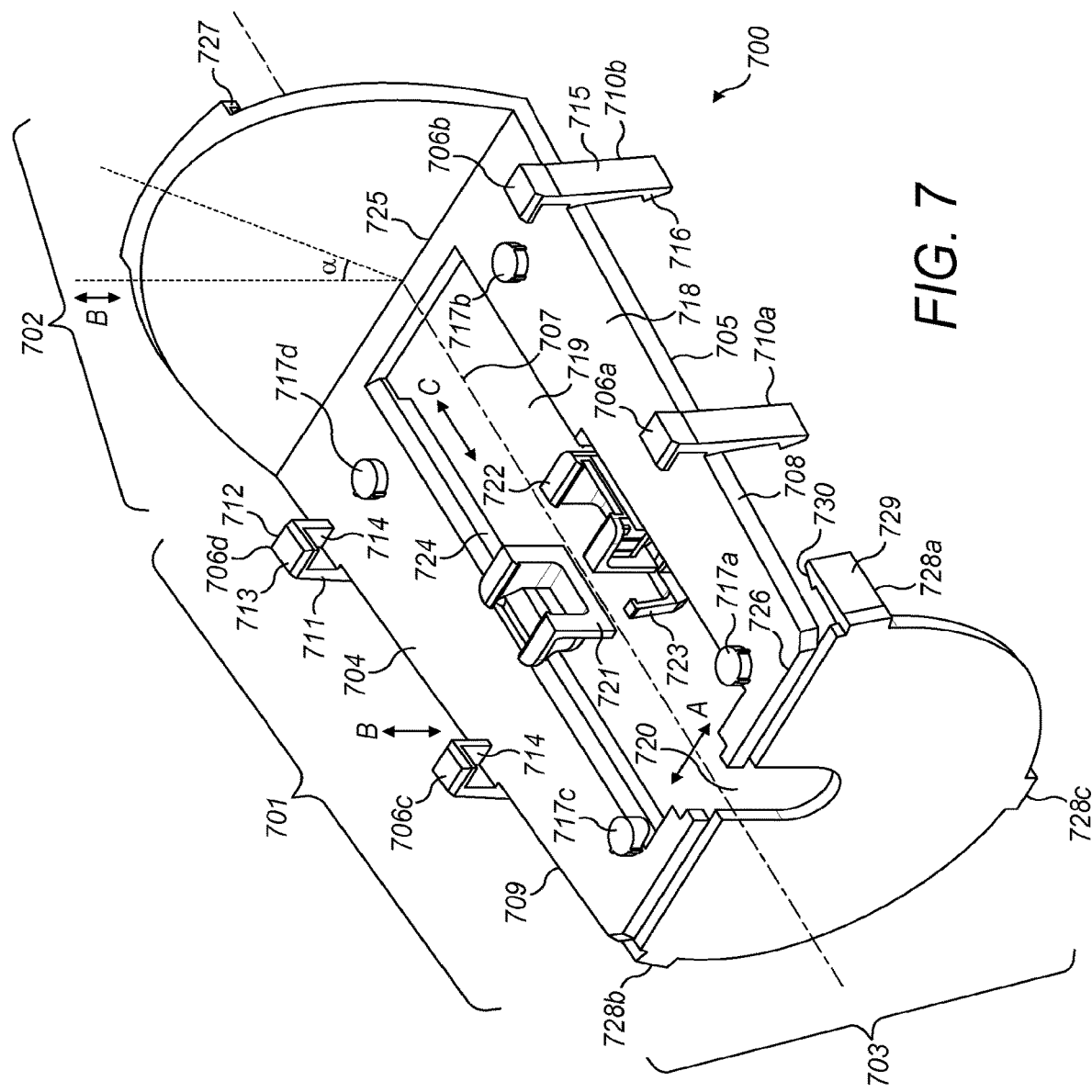
FIG. 7 illustrates an interface structure.

The sterile drape does not pass directly between the drive assembly interface 500 and the instrument interface 400. An interface structure is attached to the drape for interfacing between the drive assembly interface and the instrument interface 400. FIG. 7 shows an exemplary interface structure 700 in isolation. The interface structure 700 is also shown in FIG. 5 attached to the drive assembly interface. The interface structure 700 may be integrally formed with the drape. Alternatively, the interface structure 700 may be formed separately from the drape and subsequently attached to the drape. Either way, the interface structure 700 is sterile. One side of the interface structure 700 directly contacts the drive assembly interface. The other side of the interface structure 700 directly contacts the instrument interface. Thus, the interface structure 700 prevents the non-sterile drive assembly interface from directly touching the sterile instrument interface and hence maintains the sterile barrier between the two components.

Interface structure 700 comprises a base portion 701 and two wing portions 702, 703. Suitably, when the interface structure is attached to the surgical robot arm, the base portion 701 lies parallel to the axial direction of the terminal link of the robot arm. The base portion 701 comprises a first surface 704 which faces the surgical instrument when the instrument is attached to the robot arm (see FIG. 6). Specifically, the first surface 704 faces the instrument interface 400. The base portion 701 comprises a second surface 705 which opposes the first surface 704. The second surface 705 faces the robot arm when the instrument is attached to the robot arm (see FIG. 6). Specifically, the second surface 705 faces the drive assembly interface 500. The first surface may be flat. The second surface may be flat.

The base portion 701 supports a plurality of first fasteners 706a-d for engaging the surgical instrument so as to retain the surgical instrument to the interface structure. These first fasteners protrude from the first surface 704 of the base portion transverse to the first surface. The first fasteners protrude from the longer of the outer edges 708, 709 of the base portion. These longer edges are those which run down the length of the base portion 701. In the example of FIG. 7, there are four first fasteners. There may, however, be more than four or fewer than four first fasteners. Preferably, there are at least two first fasteners, one on either longer outer edge 708, 709, in order to prevent the instrument from dislodging from the interface structure in a direction perpendicular to the longitudinal axis 707 of the interface structure. In other words, to prevent the instrument from dislodging from the interface structure in a direction perpendicular to the longitudinal axes 508 and 408 of the terminal link of the robot arm and the instrument shaft respectively, when the instrument is engaged with the robot arm.

The base portion 701 supports a plurality of second fasteners 710a-d (only 710a and 710b shown in FIG. 7) for engaging the robot arm so as to retain the interface structure to the robot arm. These second fasteners protrude from the second surface 705 of the base portion. The second fasteners protrude from the longer of the outer edges 708, 709 of the base portion. In the example of FIG. 7, there are four second fasteners. There may, however, be more than four or fewer than four second fasteners. Preferably, there are at least two second fasteners, one on either longer outer edge 708,709, in order to prevent the interface structure from dislodging from the robot arm in a direction perpendicular to the longitudinal axis 707 of the interface structure.

The first fasteners and/or the second fasteners may be integrally formed with the base portion. In FIG. 7, each first fastener 706a-d protrudes from the same location on the outer edge of the base portion 701 as a second fastener 710a-d. Each first fastener may be integrally formed with the second fastener it is next to. In another arrangement, the first fasteners and second fasteners may protrude from different locations on the outer edge of the base portion. In FIG. 7, there are the same number of first fasteners and second fasteners. In another arrangement, there may be different numbers of first fasteners and second fasteners.

Each first fastener comprises: a body 711 which abuts an outer edge of the base portion 701; and a protrusion 712 which is the portion of the first fastener which is retained in the surgical instrument. The body 711 extends in the longitudinal direction of the interface structure. The area of the first fastener transverse to the longitudinal direction of the interface structure is shaped so as to resist force applied to it in that transverse direction. The length of the body 711 in the longitudinal direction of the interface structure is sufficient, in combination with the width of the body 711 in the direction A, to resist force applied to it in that transverse direction. The protrusion 712 is angled relative to the body 711. For example, the protrusion 712 may be perpendicular to the longitudinal axis of the body 711.

Each first fastener is shaped such that when the surgical instrument is attached to the interface structure, the first fasteners restrain the surgical instrument from moving relative to the interface structure in directions perpendicular to the longitudinal axis 707 of the interface structure. In the exemplary interface structure shown in FIG. 7, this is achieved as follows. The body 711 of the first fastener protrudes from the first surface 704 of the base portion 701 perpendicular to the surface of the base portion 701. A body of a first fastener 706a on one longer outer edge 708 of the base portion 701 in combination with a body of a further first fastener 706c on the other longer outer edge 709 of the base portion 701 thus acts to restrain the surgical instrument from moving in a transverse direction A to the longer outer edges of the base portion. A flange 713 of protrusion 712 is parallel to but spaced from the base portion 701. This spacing corresponds to that of the instrument interface component with which it engages. The flange 713 of protrusion 712 of one first fastener in combination with the base portion acts to restrain the surgical instrument from moving in a transverse direction B to the longer outer edges of the base portion.

Each first fastener is shaped such that when the surgical instrument is attached to the interface structure, the first fasteners restrain the surgical instrument from moving relative to the interface structure along the direction of the longitudinal axis 707 of the interface structure towards the rear wing portion 702. That is towards the surgical robot arm when the interface structure is attached to the surgical robot arm. In the exemplary interface structure shown in FIG. 7, this is achieved as follows. A wall 714 of protrusion 712 is transverse to flange 713 and body 711. The wall 714 abuts flange 713 and body 711. Suitably, wall 714 is perpendicular to the base portion 701. A wall 714 of a first fastener 706a on one longer outer edge 708 of the base portion 701 in combination with a wall 714 of a further first fastener 706c on the other longer outer edge 709 of the base portion 701 thus acts to restrain the surgical instrument from moving in a parallel direction C to the longer outer edges of the base portion.

Each first fastener is shaped such that when the surgical instrument is attached to the interface structure, the first fasteners permit the surgical instrument to move relative to the interface structure along the direction of the longitudinal axis 707 of the interface structure away from the rear wing portion 702. That is away from the surgical robot arm when the interface structure is attached to the surgical robot arm. In the exemplary interface structure shown in FIG. 7, this is achieved by not having any part of the first fastener impeding movement of the surgical instrument in this direction. Thus, the surgical instrument can be released from the interface structure by moving it along the direction of the longitudinal axis 707 of the interface structure away from the rear wing portion 702, thereby disengaging the first fasteners.

Each second fastener comprises: a body 715 which abuts an outer edge of the base portion 701; and a protrusion 716 which is the portion of the second fastener which is retained in the surgical robot arm. The protrusion 716 is angled relative to the body 715. Suitably, the protrusion 716 extends from the body 715 towards the base portion 701.

The second fasteners are shaped such that when the surgical instrument is detached from the surgical robot arm, the interface structure is retained in the surgical robot arm. The interface structure is more securely attached to the surgical robot arm than the instrument interface elements are to the drive assembly interface elements. Thus, the interface structure and the drape to which it is incorporated, remain attached to the surgical robot arm during instrument exchange. This is important in order to reduce the time taken to change instruments, since the interface structure does not need to be re-attached to the robot arm following detachment of an instrument. It is also important in order to reduce the likelihood of the drape tearing when changing instruments, which would cause the sterile operating environment to become contaminated with the non-sterile environment on the robot arm side of the drape. In the example of FIG. 7, this is achieved by the protrusions of each second fastener being acutely angled relative to its body. When a force is applied transverse to the base portion 701, away from the surgical robot arm, the second fasteners are more resistant to dislodging from their retained positions in the recesses of the surgical robot arm than the instrument interface elements are from dislodging from their retained positions in the drive assembly interface elements.

The interface structure may comprise alignment features to aid alignment of the surgical instrument and the surgical robot arm when they are brought into engagement. FIG. 7 illustrates alignment features 717a-d on the first surface 704 of base portion 701. The alignment features shown protrude from the first surface 704. The alignment features may, alternatively or in addition, be recessed into the first surface 704. The alignment features shown are studs. Other example alignment features include ridges and troughs. Complementary shaped alignment features on the instrument interface receive the alignment features 717a-d. Suitably, the alignment features also act to restrain movement of the instrument relative to the interface structure in the direction C parallel to the longitudinal axis 707 of the interface structure. The alignment features may act to restrain movement of the instrument relative to the interface structure in the plane of the interface structure. Preferably, the interface structure includes at least one alignment feature. More than one alignment feature may be incorporated into the interface structure, such as the four shown on FIG. 7.

The base portion 701 of the interface structure comprises a rim 718 surrounding a hollow interior 719. When the interface structure is attached to the robot arm, the rim 718 is encompassed within a boundary formed by the external surface of the surgical robot arm in the longitudinal direction of the surgical robot arm. The rim 718 has an opening 720 which receives the end of the shaft of the surgical instrument. The hollow interior 719 receives the instrument interface elements which engage with the drive assembly interface elements.

The base portion 701 may support movable covers for the drive assembly interface elements, so that the instrument interface elements do not directly contact the drive assembly interface elements, but instead engage the drive assembly interface elements via the movable covers. In the example shown in FIG. 7, movable cover 721 is configured to receive instrument interface element 403, and is received by drive assembly interface element 502. Movable cover 722 is configured to receive instrument interface element 404, and is received by drive assembly interface element 503. Movable cover 723 is configured to receive instrument interface element 405, and is received by drive assembly interface element 504. Each movable cover is a snug fit into its respective drive assembly interface element, and each movable cover snugly fits its respective instrument interface element. Thus, the drive is effectively transferred through the interface structure from the drive assembly interface to the instrument interface.

In the example of FIG. 7, the rim 718 surrounds a hollow interior 719 which houses all the moveable covers 721, 722, 723. Alternatively, the rim 718 may surround three hollow interiors, each of which houses a single one of the moveable covers.

Interface structure 700 further comprises rear wing portion 702. Rear wing portion 702 is attached to the rear edge 725 of the rim 718 of the base portion 701. Both the rear edge 725 and the front edge 726 join the two longer outer edges 708 and 709 of the base portion. When the interface structure 700 is attached to the robot arm, the front edge 726 is positioned closer to the free distal end of the robot arm than the rear edge 725. The rear wing portion 702 covers a proximal exposed surface 801 of the robot arm (see FIG. 8). Rear wing portion 702 is suitably shaped to match the shape of the proximal exposed surface 801 of the robot arm. Suitably, the rear wing portion 702 is angled relative to a direction B perpendicular to the base portion 701 away from the distal end 802 of the robot arm, by an angle α. For example, 20°<α<50°, or 30°<α<40°, or 35°<α<37°. This aids the process of passing the drape, to which the interface structure is attached, over the robot arm. The rear wing portion 702 may be integrally formed with the base portion 701. The rear wing portion 702 may be formed separately from the base portion 701. The rear wing portion 702 may be pivotally connected to the base portion 701 at rear edge 725. For example, the rear wing portion may be hinged to the base portion 701. This would enable the rear wing portion 702 and the base portion 701 to be packaged and/or stored flat relative to each other. The rear wing portion may comprise one or more third fasteners 727 for fastening the rear wing portion to the proximal exposed surface 801 of the robot arm. In the example shown in FIG. 7, the third fastener 727 is in the form of a latch which is configured to hook into a recess in the robot arm. Any suitable fastener may be used for the third fastener.

Interface structure 700 further comprises a front wing portion 703. Front wing portion 703 is attached to the front edge 726 of the rim 718 of the base portion 701. The front wing portion 703 covers a distal exposed surface 802 of the surgical robot arm (see FIG. 8). Front wing portion 703 is suitably shaped to match the shape of the distal exposed surface 802 of the robot arm. The distal exposed surface 802 of the robot arm has a hollow channel to receive the end of the instrument shaft. Thus, the front wing portion 703 suitably has the same-shaped hollow channel to receive the end of the instrument shaft. The front wing portion 703 may be perpendicular to the base portion 701 when attached to the robot arm. The front wing portion 703 may be integrally formed with the base portion 701. The front wing portion 703 may be formed separately from the base portion 701. The front wing portion 703 may clip onto the base portion 701. The front wing portion 703 may be pivotally connected to the base portion 701 at front edge 726. For example, the front wing portion may be hinged to the base portion 701. This would enable the front wing portion 703 and the base portion 701 to be packaged and/or stored flat relative to each other. The front wing portion 703 may comprise one or more fourth fasteners 728*a-c* for fastening the front wing portion to the distal exposed surface 802 of the robot arm. In the example of FIG. 7, each fourth fastener has the same form as the second fasteners previously described. If the front wing portion 703 is perpendicular to the base portion 701 when attached to the surgical robot arm, then when the interface structure is attached to the surgical robot arm the fourth fasteners 728*a-c* are perpendicular to the first and second fasteners.

Figure 10:
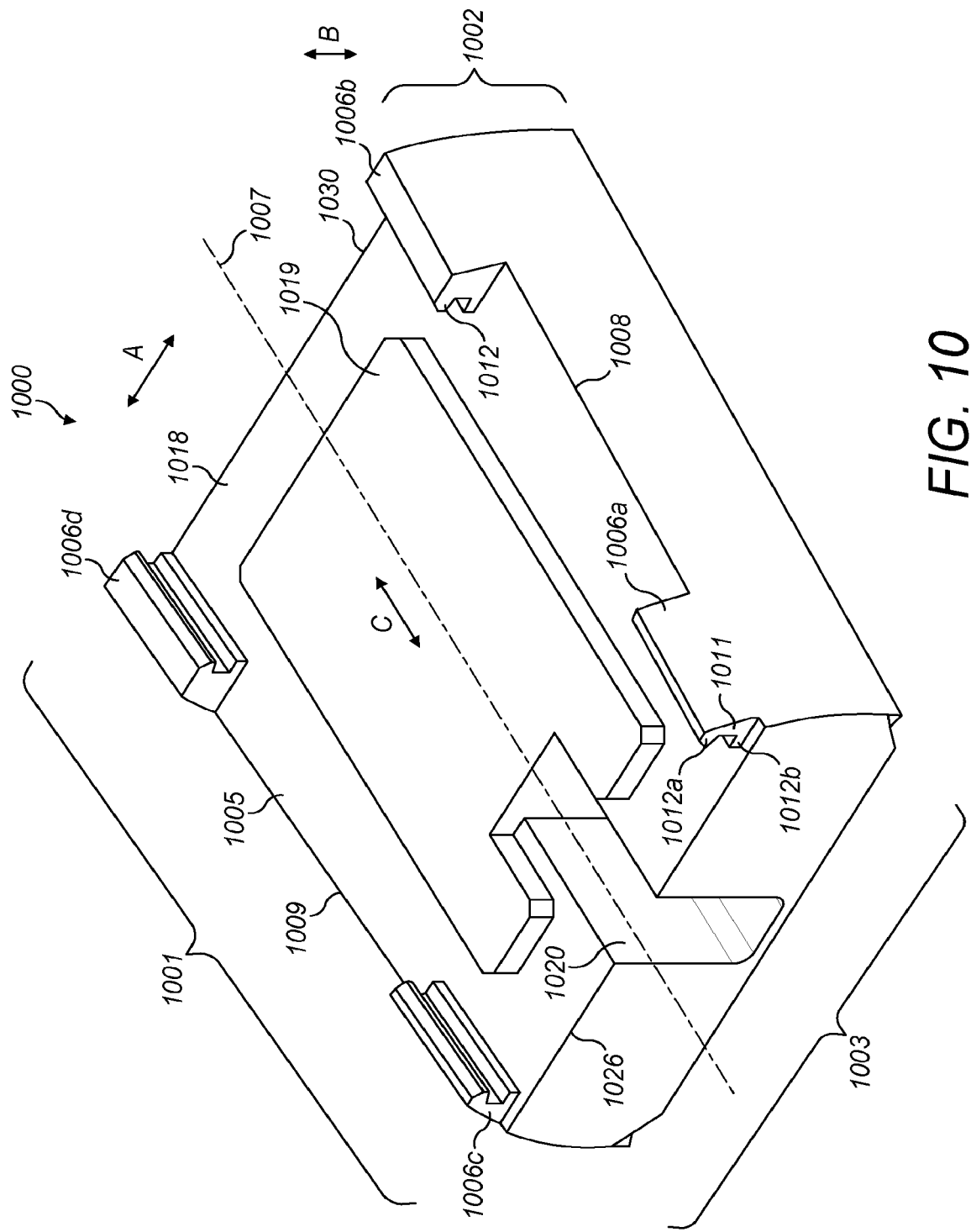
FIG. 10 illustrates a further interface structure.

FIG. 10 shows a further exemplary interface structure 1000 in isolation. The interface structure 1000 may be integrally formed with the drape. Alternatively, the interface structure 1000 may be formed separately from the drape and subsequently attached to the drape. Either way, the interface structure 1000 is sterile. One side of the interface structure 1000 directly contacts the drive assembly interface. The other side of the interface structure 1000 directly contacts the instrument interface. Thus, the interface structure 1000 prevents the non-sterile drive assembly interface from directly touching the sterile instrument interface and hence maintains the sterile barrier between the two components.

Interface structure 1000 comprises a base portion 1001, a front wing portion 1003, and two side flange portions 1002, 1004. The interface structure 1000 may also comprise a rear wing portion (not shown) having the same shape and features as the rear wing portion 702 described with respect to FIG. 7. Suitably, when the interface structure is attached to the surgical robot arm, the base portion 1001 lies parallel to the axial direction of the terminal link of the robot arm. The base portion 1001 comprises a first surface 1005 which faces the surgical instrument when the instrument is attached to the robot arm. Specifically, the first surface 1005 faces the instrument interface 400. The base portion 1001 comprises a second surface which opposes the first surface 1005. The second surface faces the robot arm when the instrument is attached to the robot arm. Specifically, the second surface faces the drive assembly interface. The first surface may be flat. The second surface may be flat.

The base portion 1001 supports a plurality of first fasteners 1006*a-d* for engaging the surgical instrument so as to retain the surgical instrument to the interface structure. These first fasteners protrude from the first surface 1005 of the base portion transverse to the first surface. The first fasteners protrude from the longer of the outer edges 1008, 1009 of the base portion. These longer edges are those which run down the length of the base portion 1001. These longer edges are those which connect the first surface and the side flange portions. In the example of FIG. 10, there are four first fasteners. There may, however, be more than four or fewer than four first fasteners. Preferably, there are at least two first fasteners, one on either longer outer edge 1008, 1009, in order to prevent the instrument from dislodging from the interface structure in a direction perpendicular to the longitudinal axis 1007 of the interface structure. In other words, to prevent the instrument from dislodging from the interface structure in a direction perpendicular to the longitudinal axes 508 and 408 of the terminal link of the robot arm and the instrument shaft respectively, when the instrument is engaged with the robot arm.

The base portion 1001 supports a plurality of second fasteners (not shown in FIG. 10) for engaging the robot arm so as to retain the interface structure to the robot arm. Each second fastener may be integrally formed with a side flange portion 1002, 1004. Each second fastener may protrude from an opposing edge of the side flange portion to that which the first fasteners protrude from. There may be four second fasteners. There may, however, be more than four or fewer than four second fasteners. Preferably, there are at least two second fasteners, one protruding from each side flange portion 1002, 1004, in order to prevent the interface structure from dislodging from the robot arm in a direction perpendicular to the longitudinal axis 1007 of the interface structure.

The first fasteners may be integrally formed with the base portion. There may be the same number of first fasteners and second fasteners. There may be different numbers of first fasteners and second fasteners.

Each first fastener comprises: a body 1011 and a protrusion 1012. The body 1011 extends in a direction transverse to the first surface 1005. In the example of FIG. 10, the body 1011 extends wholly from the first surface 1005 and abuts an edge connecting the base portion 1001 and the side flange portion 1002. However, the body 1001 may project wholly from the first surface 1005 of the base portion 1001 and not abut the edge connecting the base portion 1001 and the side flange portion 1002. The body 1011 extends in the longitudinal direction of the interface structure. The area of the first fastener transverse to the longitudinal direction of the interface structure is shaped so as to resist force applied to it in that transverse direction. The length of the body 1011 in the longitudinal direction of the interface structure is sufficient, in combination with the width of the body 1011 in the direction A, to resist force applied to it in that transverse direction. The protrusion 1012 is retained in the surgical instrument. The protrusion 1012 may comprise protruding elements 1012a, 1012b, each of which is retained in the surgical instrument. The protrusion 1012 is angled relative to the body 1011. For example, the protrusion 1012 may be perpendicular to the longitudinal axis of the body 1011.

Each first fastener is shaped such that when the surgical instrument is attached to the interface structure, the first fasteners restrain the surgical instrument from moving relative to the interface structure in directions perpendicular to the longitudinal axis 1007 of the interface structure. In the exemplary interface structure shown in FIG. 10, this is achieved as follows. The body 1011 of the first fastener protrudes from the first surface 1005 of the base portion 1001 perpendicular to the surface of the base portion 1001. A body of a first fastener 1006a on one side of the base portion 1001 in combination with a body of a further first fastener 1006c on the other side of the base portion 1001 thus acts to restrain the surgical instrument from moving in a transverse direction A to the longer outer edges of the base portion. The protruding elements 1012a, 1012b may be parallel to the base portion 1001. The protruding elements 1012a, 1012b may be spaced by a spacing which corresponds to that of the instrument interface component with which it engages. The protruding elements 1012a, 1012b act to restrain the surgical instrument from moving in a transverse direction B to the longer outer edges of the base portion.

Each first fastener may be shaped such that when the surgical instrument is attached to the interface structure, the first fasteners restrain the surgical instrument from moving relative to the interface structure along the direction of the longitudinal axis 1007 of the interface structure away from the front wing portion 1003. That is towards the surgical robot arm when the interface structure is attached to the surgical robot arm. Not shown in FIG. 10, each first fastener may comprise a wall which is transverse to the protrusion 1012 and the body 1011. The wall abuts protrusion 1012 and body 1011. Suitably, the wall is perpendicular to the base portion 1001. A wall of a first fastener 1006a on one longer outer edge 1008 of the base portion 1001 in combination with a wall of a further first fastener 1006c on the other longer outer edge 1009 of the base portion 1001 thus acts to restrain the surgical instrument from moving in a parallel direction C to the longer outer edges of the base portion.

Each second fastener comprises a protrusion which is the portion of the second fastener which is retained in the surgical robot arm. The protrusion is angled relative to the side flange portion. Suitably, the protrusion extends from the side flange portion towards the base portion 1001.

The second fasteners are shaped such that when the surgical instrument is detached from the surgical robot arm, the interface structure is retained in the surgical robot arm. The interface structure is more securely attached to the surgical robot arm than the instrument interface elements are to the drive assembly interface elements. Thus, the interface structure and the drape to which it is incorporated, remain attached to the surgical robot arm during instrument exchange. This is important in order to reduce the time taken to change instruments, since the interface structure does not need to be re-attached to the robot arm following detachment of an instrument. It is also important in order to reduce the likelihood of the drape tearing when changing instruments, which would cause the sterile operating environment to become contaminated with the non-sterile environment on the robot arm side of the drape. In the example of FIG. 10, this is achieved by the protrusions of each second fastener being acutely angled relative to the side flange portion. When a force is applied transverse to the base portion 1001, away from the surgical robot arm, the second fasteners are more resistant to dislodging from their retained positions in the recesses of the surgical robot arm than the instrument interface elements are from dislodging from their retained positions in the drive assembly interface elements.

The interface structure may comprise alignment features to aid alignment of the surgical instrument and the surgical robot arm when they are brought into engagement. These alignment features are as described with respect to FIG. 7.

The base portion 1001 of the interface structure comprises a rim 1018 surrounding a hollow interior 1019. When the interface structure is attached to the robot arm, the rim 1018 is encompassed within a boundary formed by the external surface of the surgical robot arm in the longitudinal direction of the surgical robot arm. The rim 1018 has an opening 1020 which receives the end of the shaft of the surgical instrument. The hollow interior 1019 receives the instrument interface elements which engage with the drive assembly interface elements.

The base portion 1001 may support movable covers (not shown) for the drive assembly interface elements, so that the instrument interface elements do not directly contact the drive assembly interface elements, but instead engage the drive assembly interface elements via the movable covers. These movable covers are as described with reference to FIG. 7. The rim 1018 may surround a hollow interior 1019 which houses all the moveable covers. Alternatively, the rim 1018 may surround three hollow interiors, each of which houses a single one of the moveable covers.

Interface structure 700 further comprises a front wing portion 1003. Front wing portion 1003 is attached to the front edge 1026 of the rim 1018 of the base portion 1001. The front wing portion 1003 covers a distal exposed surface of the surgical robot arm. Front wing portion 1003 is suitably shaped to match the shape of the distal exposed surface of the robot arm. The distal exposed surface of the robot arm has a hollow channel to receive the end of the instrument shaft. Thus, the front wing portion 1003 suitably has the same-shaped hollow channel to receive the end of the instrument shaft. The front wing portion 1003 may be perpendicular to the base portion 1001 when attached to the robot arm. The front wing portion 1003 may be integrally formed with the base portion 1001. The front wing portion 1003 may be formed separately from the base portion 1001. The front wing portion 1003 may clip onto the base portion 1001. The front wing portion 1003 may be pivotally connected to the base portion 1001 at front edge 1026. For example, the front wing portion may be hinged to the base portion 1001. This would enable the front wing portion 1003 and the base portion 1001 to be packaged and/or stored flat relative to each other.

Figure 14:
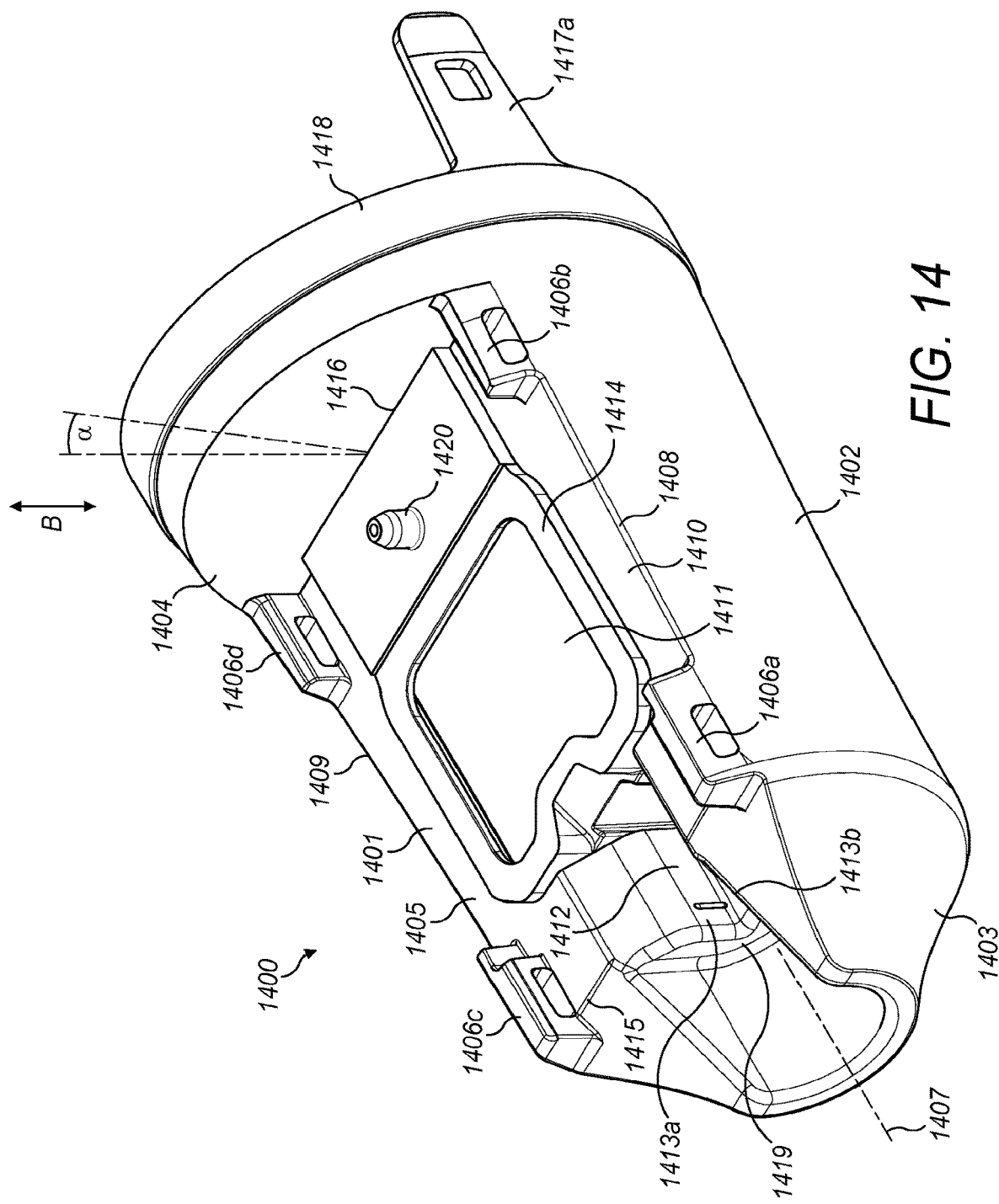
FIG. 14 illustrates a further interface structure.

FIG. 14 shows a further exemplary interface structure 1400 in isolation. Suitably, the interface structure 1400 is a single moulded part. The interface structure 1400 may be integrally formed with the drape. Alternatively, the interface structure 1400 may be formed separately from the drape and subsequently attached to the drape. Either way, the interface structure 1400 is sterile. One side of the interface structure 1400 directly contacts the drive assembly interface. Another side of the interface structure 1400 directly contacts the instrument interface. Thus, the interface structure 1400 prevents the non-sterile drive assembly interface from directly touching the sterile instrument interface and hence maintains the sterile barrier between the two components.

Interface structure 1400 comprises a base portion 1401 and an envelope portion 1402. The interface structure 1400 may also comprise a front wing portion 1403. The interface structure may further comprise a rear wing portion 1404. Suitably, when the interface structure is attached to the surgical robot arm, the base portion 1401 lies parallel to the axial direction of the terminal link of the robot arm. The base portion 1401 comprises a first surface 1405 which faces the surgical instrument when the instrument is attached to the robot arm. Specifically, the first surface 1405 faces the instrument interface 400. The base portion 1401 comprises a second surface (not visible on FIG. 14) which opposes the first surface 1405. The second surface faces the robot arm when the instrument is attached to the robot arm. Specifically, the second surface faces the drive assembly interface. The first surface may be flat. The second surface may be flat.

The base portion 1401 supports a plurality of first fasteners 1406*a-d* for engaging the surgical instrument so as to retain the surgical instrument to the interface structure. These first fasteners, and their relationship to the base portion 1401, are as described with respect to the first fasteners 1006*a-d* and base portion 1001 of FIG. 10.

The envelope portion 1402 connects the longer of the outer edges 1408, 1409 of the base portion. These longer edges are those which run down the length of the base portion 1401. As shown in FIG. 14, the envelope portion may circumscribe the drive assembly. The shape of the envelope portion 1402 may match the shape of the outer surface of the robot arm at the drive assembly. Suitably, the envelope portion 1402 contacts the exterior surface of the robot arm at the drive assembly. This contact may be a snug fit. This contact may be sheath-like. In this way, the envelope portion 1402 bears on the exterior surface of the robot arm at the drive assembly. The envelope portion 1402 thereby acts to retain the interface structure 1400 to the robot arm. Specifically, the envelope portion 1402 acts to retain the interface structure 1400 to the robot arm in directions transverse to the longitudinal axis 1407 of the interface structure 1400.

When the surgical instrument is detached from the surgical robot arm, the interface structure 1400 is retained in the surgical robot arm. The interface structure is more securely attached to the surgical robot arm than the instrument interface elements are to the drive assembly interface elements. Thus, the interface structure and the drape, remain attached to the surgical robot arm during instrument exchange. This is important in order to reduce the time taken to change instruments, since the interface structure does not need to be re-attached to the robot arm following detachment of an instrument. It is also important in order to reduce the likelihood of the drape tearing when changing instruments, which would cause the sterile operating environment to become contaminated with the non-sterile environment on the robot arm side of the drape. In the example of FIG. 14, this is achieved by the shape of the envelope portion 1402 surrounding the exterior of the robot arm at the drive assembly, and by the envelope portion 1402 connecting to the base portion 1401 wholly along the length of the sides 1408 and 1409. When a force is applied transverse to the base portion 1401, away from the surgical robot arm, the envelope portion 1402 is more resistant to breaking and hence dislodging from its retained position relative to the surgical robot arm than the instrument interface elements are from dislodging from their retained positions in the drive assembly interface elements.

Figure 15:
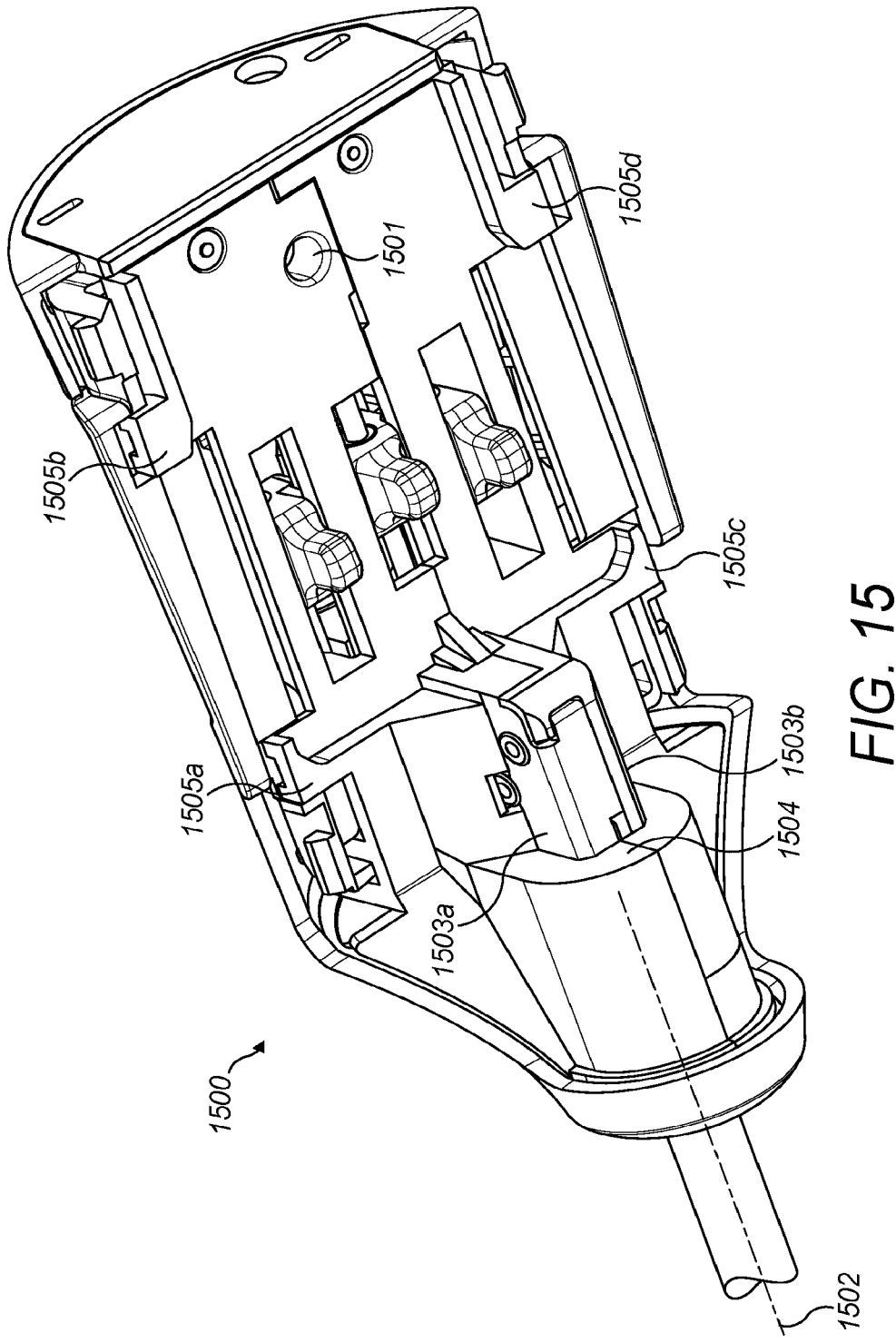
FIG. 15 illustrates a further instrument interface.

The interface structure may comprise alignment features to aid alignment of the surgical instrument and the surgical robot arm when they are brought into engagement. These alignment features may be as described with respect to FIG. 7. For example, the base portion 1401 may comprise a pin 1420. Pin 1420 may be located on the longitudinal axis 1407 of the interface structure 1400. FIG. 15 illustrates an exemplary instrument interface 1500 which engages the interface structure 1400. Instrument interface 1500 comprises a recess 1501 into which the pin 1420 of the interface structure 1400 engages. Recess 1501 may be located on the longitudinal axis 1502 of the instrument interface 1500. The pin 1420 fits snugly into the recess 1501. The instrument interface 1500 of FIG. 15 contacts the base portion 1401 of the interface structure at the seat areas 1505*a*, 1505*b*, 1505*c*, 1505*d*.

The base portion 1401 of the interface structure comprises a rim 1410 surrounding a hollow interior 1411. When the interface structure is attached to the robot arm, the rim 1410 is encompassed within a boundary formed by the external surface of the surgical robot arm in the longitudinal direction of the surgical robot arm. The rim 1410 has an opening 1412 which receives the portion of the chassis of the instrument interface 1500 into which the end of the shaft of the surgical instrument terminates. The opening 1412 is valley-shaped, with valley walls 1413*a* and 1413*b*. The instrument interface 1500 has contact faces 1503*a* and 1503*b*, which have a complementary shape to the valley walls 1413*a,b* such that contact faces 1503*a,b* engage valley walls 1413*a,b* when the instrument interface is engaged in the interface structure. Suitably, the contact faces 1503*a,b* have a light interference fit to the valley walls 1413*a,b*. The engagement of the contact faces and valley walls acts to prevent motion of the instrument parallel to the base portion 1401 and transverse to the longitudinal axis of the interface structure 1407. The engagement of the contact faces and valley walls acts to prevent rotational motion of the instrument about the longitudinal axis of the interface structure 1407. The instrument interface 1500 suitably has a contact face 1504 which abuts a contact face 1419 of the opening 1412 when the instrument interface is engaged in the interface structure. The contact face 1419 is transverse to the longitudinal axis 1407. The contact face 1419 is parallel to the front edge 1415 of the base portion. The front edge 1415 joins the two longer outer edges 1408 and 1409 of the base portion. The engagement of the pin 1420 in the recess 1501, and the bearing of the contact face 1504 on the contact face 1419 cause the instrument to be aligned axially with the interface structure. They also act to restrain movement of the instrument relative to the interface structure in the axial direction.

The hollow interior 1411 receives the instrument interface elements which engage with the drive assembly interface elements. Suitably, a flexible material covers the hollow interior 1411. The flexible material is bonded to the rim 1414 of the hollow interior 1411. In this way, the flexible material provides a sterile barrier between the instrument interface elements and the drive assembly interface elements. The flexible material may be composed of kraton.

Alternatively, the base portion 1401 may support movable covers (not shown) for the drive assembly interface elements, so that the instrument interface elements do not directly contact the drive assembly interface elements, but instead engage the drive assembly interface elements via the movable covers. These movable covers are as described with reference to FIG. 7. The rim 1410 may surround a hollow interior 1411 which houses all the moveable covers. Alternatively, the rim 1410 may surround three hollow interiors, each of which houses a single one of the moveable covers.

Interface structure 1400 further comprises a front wing portion 1403. Front wing portion 1403 is attached to the front edge 1415 of the rim 1410 of the base portion 1401. Suitably, the front wing portion 1403 is integrally moulded with the base portion and envelope portion of the interface structure. The front wing portion 1403 covers a distal exposed surface of the surgical robot arm. Front wing portion 1403 may be shaped to match the shape of the distal exposed surface of the robot arm.

Interface structure 1400 further comprises rear wing portion 1404. Rear wing portion 1404 is attached to the rear edge 1416 of the rim 1410 of the base portion 1401. Both the rear edge 1416 and the front edge 1415 join the two longer outer edges 1408 and 1409 of the base portion. When the interface structure 1400 is attached to the robot arm, the front edge 1415 is positioned closer to the free distal end of the robot arm than the rear edge 1416. The rear wing portion 1404 covers a proximal exposed surface of the robot arm. Rear wing portion 1404 is suitably shaped to match the shape of the proximal exposed surface of the robot arm.

Suitably, the rear wing portion 1404 is angled relative to a direction B perpendicular to the base portion 1401 away from the distal end of the robot arm, by an angle α. For example, 20°<α<50°, or 30°<α<40°, or 35°<α<37°. This aids the process of passing the drape, to which the interface structure is attached, over the robot arm. The rear wing portion 1404 may be integrally moulded with the base portion 1401 and the envelope portion 1402.

Figure 16:
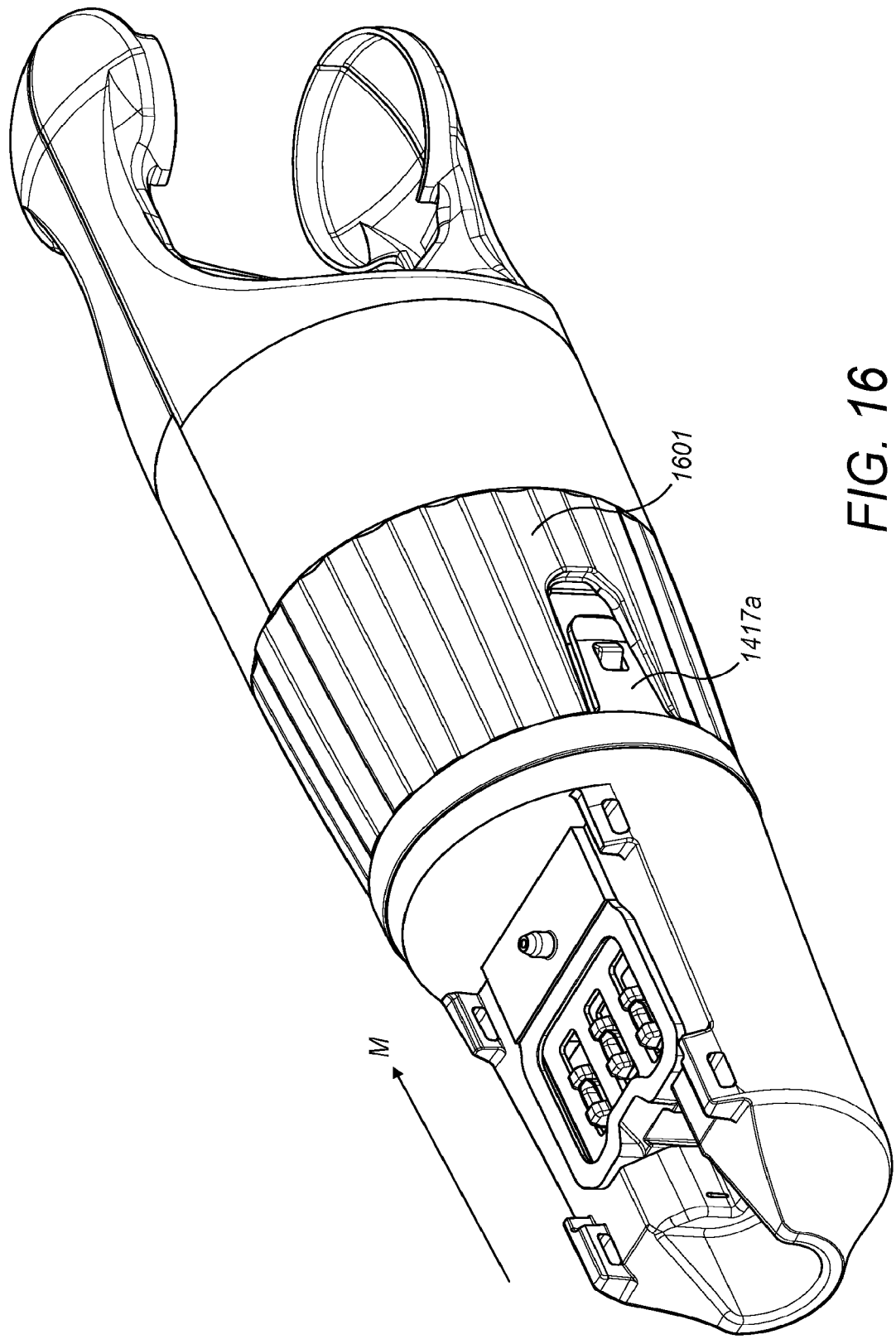
FIG. 16 illustrates the interface structure of FIG. 14 attached to a robot arm.

The rear wing portion may comprise one or more third fasteners 1417 for fastening the rear wing portion to the proximal exposed surface of the robot arm. In the example shown in FIG. 14, there are two third fasteners 1417a, 1417b (1417b is not visible in the figure) which are each in the form of a clip which is configured to clip onto a lug of a slip collar of the robot arm (see FIG. 16). Any suitable fastener may be used for the third fastener.

The interface structure 1400 may comprise features on its interior surfaces for interacting with the robot arm. For example, the interface structure 1400 may comprise an interior feature for biasing the interface structure axially against the robot arm. This interior feature may be a biasing material located on the interior surface of the front wing portion 1403. This biasing material may, for example, be a resilient foam material. When the interface structure 1400 is installed on the end of the robot arm, the biasing material pushes the interface structure 1400 against the robot arm, such that each third fastener is pushed against the mounting feature of the robot arm onto which it mounts. This acts to resist motion between the interface structure and the robot arm.

The interface structure 1400 may comprise ribs on the interior surface of the envelope portion 1402. These ribs may engage in complementary shaped recesses in the exterior surface of the robot arm at the drive assembly, when the interface structure 1400 is attached to the robot arm. These ribs act to resist motion between the interface structure and the robot arm.

For both the interface structure described with reference to FIG. 7 and the interface structure described with reference to FIG. 10, the outer boundary of the interface structure terminates in a sterile drape (not shown). The sterile drape shrouds the surgical robot arm. The inner boundary of the interface structure may terminate in a sterile membrane (not shown) which extends over the hollow interior to isolate the sterile environment from the non-sterile drive assembly.

For the interface structure described with reference to FIG. 14, collar 1418 of the interface structure terminates in a sterile drape (not shown). The collar 1418 is attached to the rear wing portion 1404 and the envelope portion 1402. Suitably, the collar 1418 is integrally moulded with the rear wing portion 1404 and the envelope portion 1402. In the example of FIG. 14, the collar is a cylindrical surface. The sterile drape shrouds the surgical robot arm. In practice, the interface structure 1400 is installed axially onto the robot arm, i.e. along the longitudinal axis of the drive assembly interface at the end of the robot arm. The drape is then unravelled down the robot arm. The combination of the interface structure and sterile drape form a continuous sterile barrier, such that when the interface structure and sterile drape are attached to the robot arm, no part of the robot arm is exposed to the instrument facing side of the interface structure.

For both the interface structure described with reference to FIG. 7, the interface structure described with reference to FIG. 10, and the interface structure described with reference to FIG. 14, the interface structure may further include a wireless receiver for receiving wireless transmissions from the surgical instrument. Preferably, the wireless receiver operates according to a communications protocol which has a short range, for example NFC, WiFi or Bluetooth. The receiver receives transmissions relating to the surgical instrument. For example, the receiver may receive transmissions relating to one or more of the following attributes of the surgical instrument: identity, type, origin, status, number of times used, length of time used, number of times left to use before expiry, length of time left to use before expiry. The wireless receiver may be located anywhere on the interface structure. Preferably, it is located on the side of the interface structure which faces the surgical robot arm. For example, in the interface structure of FIG. 7, the wireless receiver may be located on the robot arm facing surface of the rear wing portion. The wireless receiver may be a wireless transceiver which also incorporates a transmitter for transmitting wireless transmissions to the surgical instrument.

Figure 8:
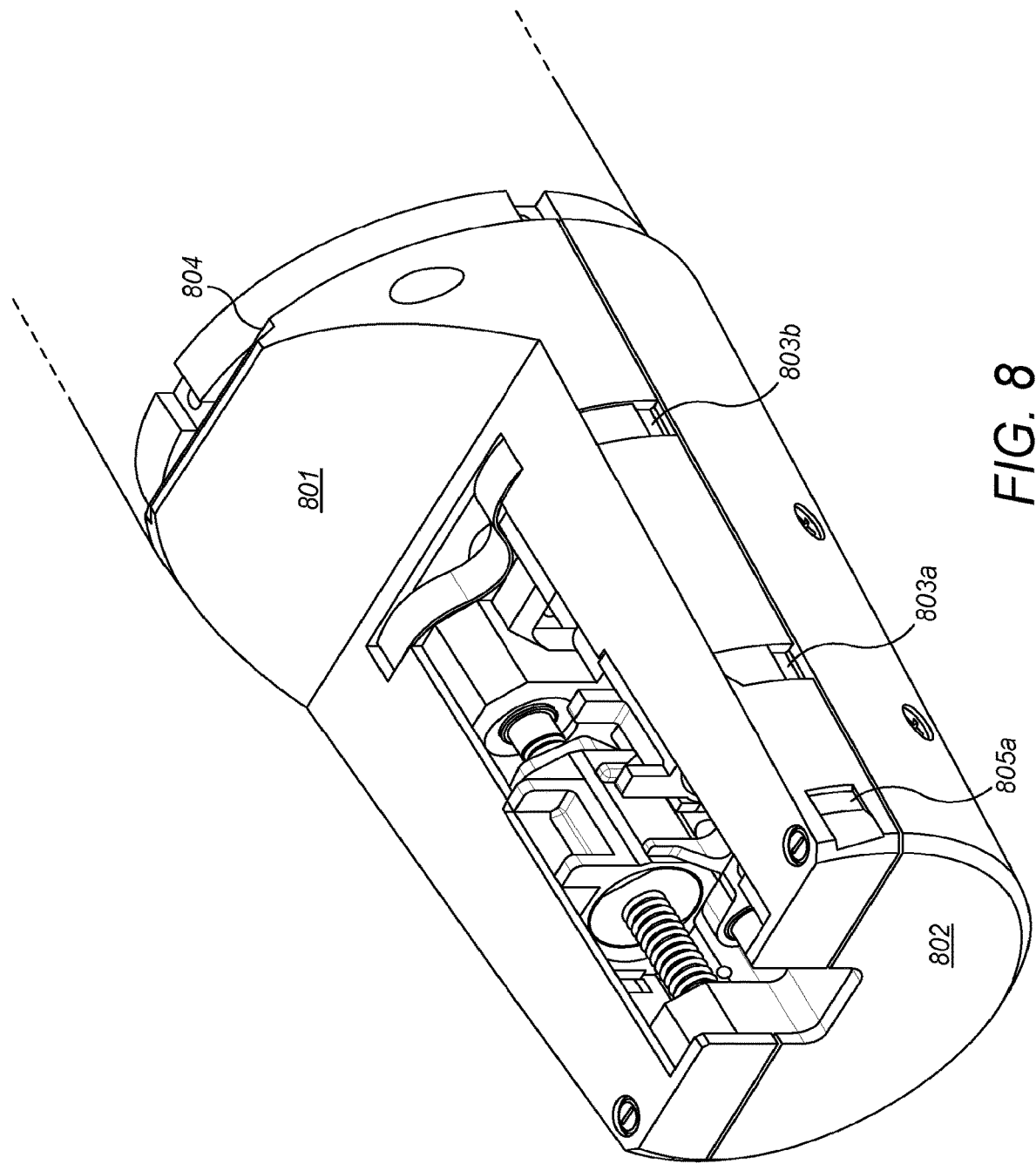
FIG. 8 illustrates a drive assembly interface of a robot arm.

FIG. 8 illustrates the end of a robot arm without the interface structure 700 of FIG. 7 attached. The robot arm comprises recesses 803a-d (only 803a and 803b shown)

which are arranged to retain the second fasteners 710a-d of the interface structure. The recesses 803a-d are a complementary shape to the second fasteners 710-a-d. Thus, each second fastener 710 fits snugly into its respective recess 803, thereby preventing the interface structure from moving in any direction relative to the surgical robot arm when they are engaged.

The robot arm comprises recess 804 which is arranged to retain the third fastener 727 of the interface structure. The recess 804 is a complementary shape to the third fastener 727. Thus the third fastener 727 fits snugly into recess 804. In the example of FIGS. 7 and 8, the recess 804 comprises a ledge over which the latch 727 hooks.

The robot arm comprises recesses 805a-c (only 805a shown) which are arranged to retain the fourth fasteners 728a-c of the interface structure. The recesses 805a-c are a complementary shape to the fourth fasteners 728a-c. Thus, each fourth fastener 728 fits snugly into its respective recess 805. The fourth fasteners 728a-c being retained in recesses 805a-c constrain the interface structure (and hence the attached surgical instrument) from moving along the longitudinal axis 508 of the terminal link of the robot arm. Thus, this arrangement stops the surgical instrument from shifting along the longitudinal axis 508 of the drive assembly as the drive assembly interface elements are driven along the direction of the longitudinal axis 508.

The number and location of the recesses in the surgical robot arm matches the number and location of second, third and fourth fasteners on the interface structure. In the implementation of FIG. 8, there are four recesses 803a-d to match the four second fasteners 710a-d shown in FIG. 7. However, there may be more than or fewer than four recesses 803a-d. In the implementation of FIG. 8, there is one recess 804 to match the third fastener 727 of FIG. 7. However, there may be more than one recess 804. In the implementation of FIG. 8, there are three recesses 805a-c to match the three fourth fasteners 728a-c shown in FIG. 7. However, there may be more than or fewer than three recesses 805a-c.

A similar robot arm to that described with respect to FIG. 8 is configured to receive the interface structure 1000 of FIG. 10. This robot arm comprises recesses arranged to retain the second fasteners of the interface structure 1000. These recesses are a complimentary shape to the second fasteners. Thus, each second fastener fits snugly into its respective recess, thereby preventing the interface structure from moving in any direction relative to the surgical robot arm when they are engaged. The robot arm comprises a detent which the rear edge 1030 of the interface structure 1000 pushes back over in order to engage the interface structure with the robot arm. The robot arm may comprise further recesses. The number and location of the recesses in the surgical robot arm match the number and location of the fasteners on the interface structure 1000.

Figure 9:
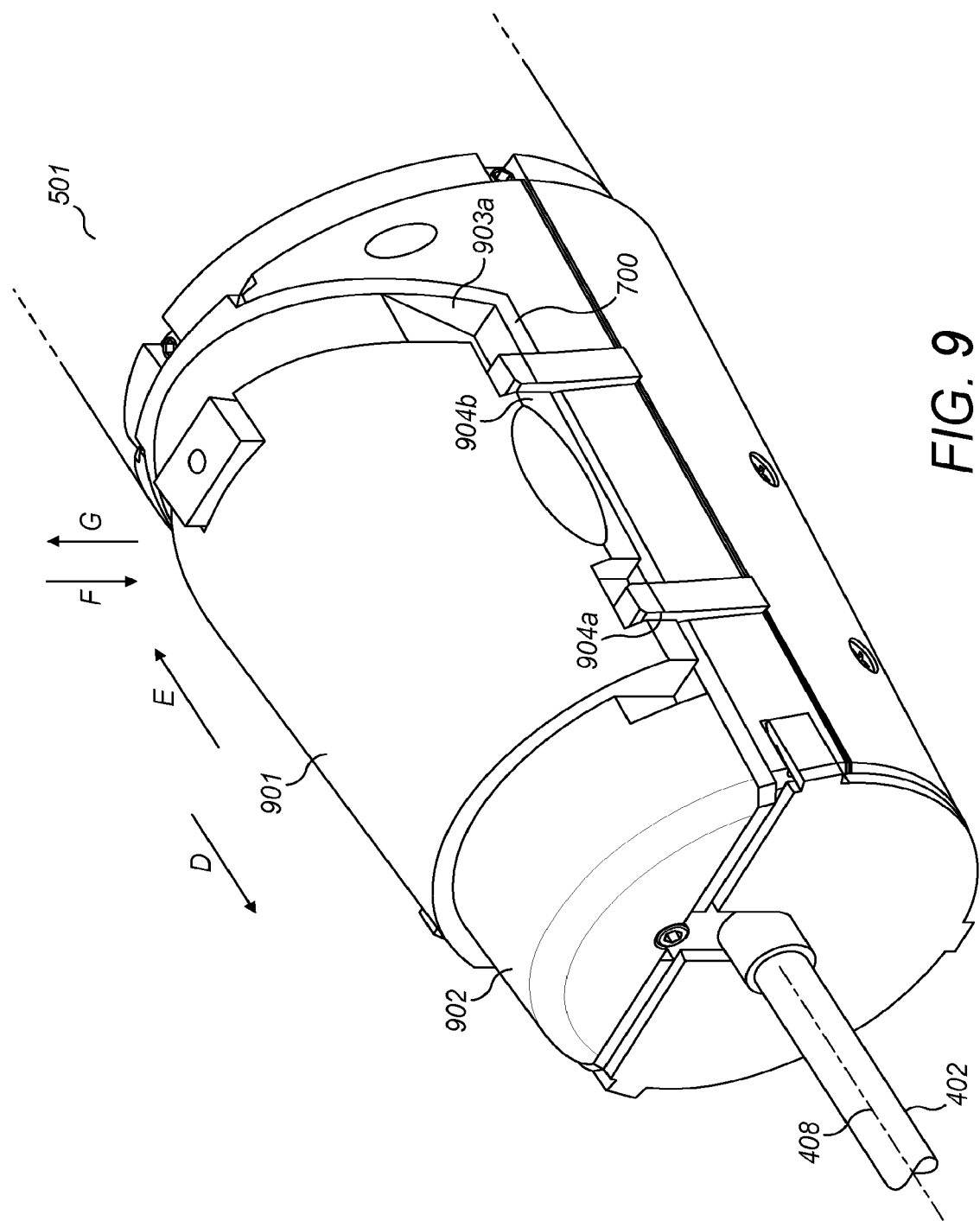
FIG. 9 illustrates an instrument attached to a robot arm via the interface structure of FIG. 7.

FIG. 9 illustrates an engaged configuration of a surgical robot arm and a surgical instrument, in which the surgical instrument is attached to the surgical robot arm via the interface structure 700 of FIG. 7. In the example of FIG. 9, the surgical instrument comprises a body 902 and an engagement portion 901, both of which cover the instrument interface 400 shown in FIGS. 4 and 6. The engagement portion is displaceable relative to the body along the direction of the longitudinal axis of the instrument shaft 408.

The body 902 comprises at least two recesses 903a-b (only 903a shown), each recess configured to receive at least one first fastener 706a-d of the interface structure. In the engaged configuration shown in FIG. 9, at least one recess is aligned with the outer edge 708 of the base portion 701, and configured to receive at least one first fastener that protrudes from the outer edge 708 of the base portion 701. In the engaged configuration shown in FIG. 9, at least one recess is aligned with the opposing outer edge 709 of the base portion 701, and configured to receive at least one first fastener that protrudes from the outer edge 709 of the base portion 701. In an alternative implementation, the body 902 may comprise a recess 903 per first fastener 706. The number and location of the recesses 903 complement the first fasteners 706.

The engagement portion 901 is moveable between a disengaged position in which the instrument can be lifted free from the interface structure, and an engaged position in which the instrument cannot be lifted free from the interface structure. When the engagement portion 901 is at the end of its displaceable range most proximal to the end effector of the surgical instrument, the engagement portion is in the disengaged position. When the engagement portion 901 is at the end of its displaceable range most distal from the end effector of the surgical instrument, the engagement portion is in the engaged position.

The engagement portion comprises a plurality of nibs 904a-d, each of which is configured to engage a first fastener of the interface structure in the engaged configuration. Each nib 904 is of a complementary shape to the first fastener 706. In the example of FIGS. 7 and 9, each nib has a plug shape thereby enabling it to engage into the socket formed by the combination of the first fastener 706 and the base portion 701 of the engagement structure.

Figure 11:
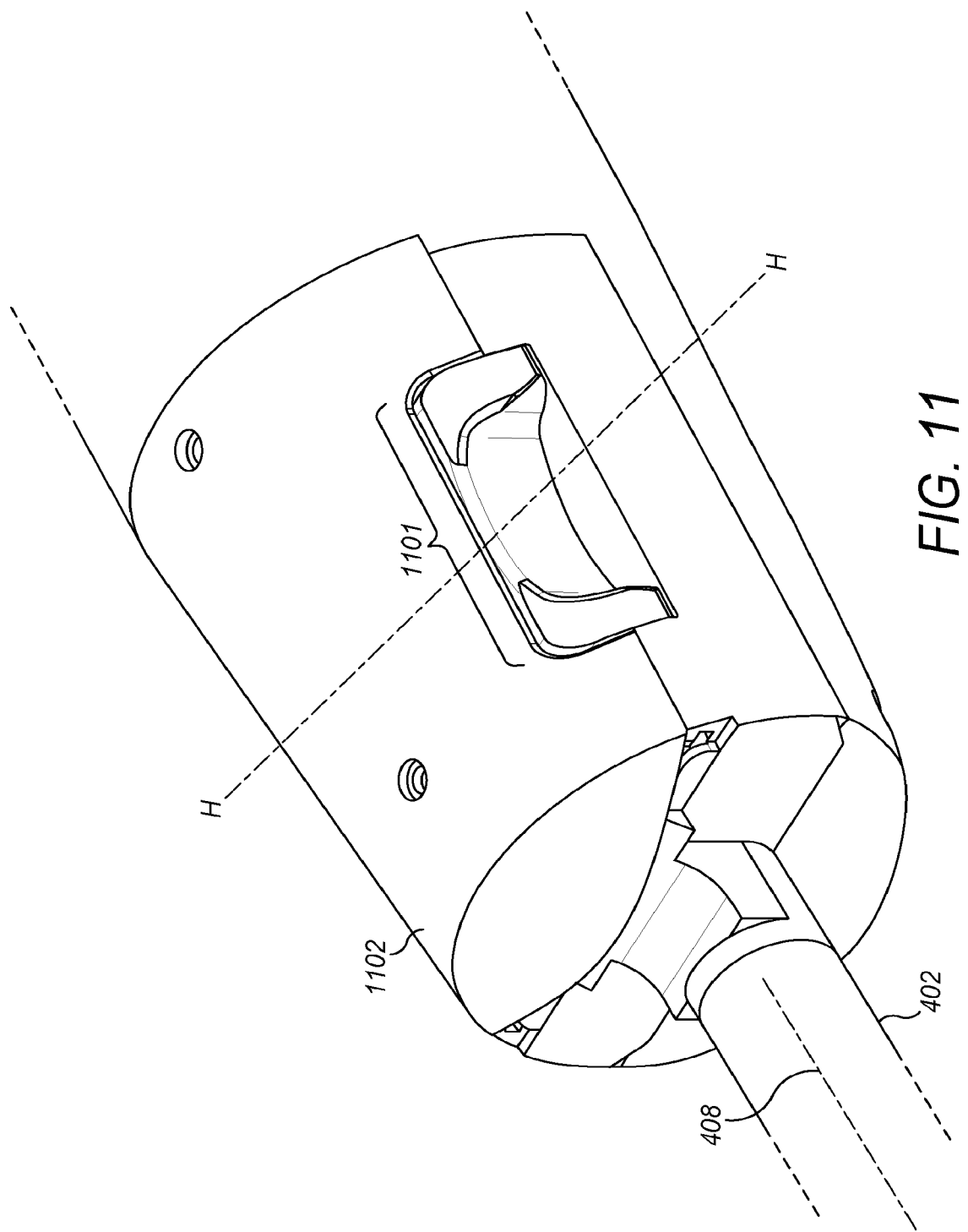
FIG. 11 illustrates an instrument attached to a robot arm via the interface structure of FIG. 10.

FIG. 11 illustrates an engaged configuration of a surgical robot arm and a surgical instrument, in which the surgical instrument is attached to the surgical robot arm via the interface structure 1000 of FIG. 10. In the example of FIG. 11, the surgical instrument comprises a body 1102 and two engagement portions 1101 (one shown), all of which cover the instrument interface 400 shown in FIGS. 4 and 6. The engagement portions are on opposing sides of the instrument interface. One engagement portion engages the first fasteners on one side of the instrument interface, and the other engagement portion engages the first fasteners on the other side of the instrument interface. Each engagement portion is displaceable relative to the body along the direction A shown in FIG. 10 which is transverse to the longitudinal axis of the instrument shaft 408. Each engagement portion is displaceable along the direction A towards the interior of the instrument.

Figure 12:
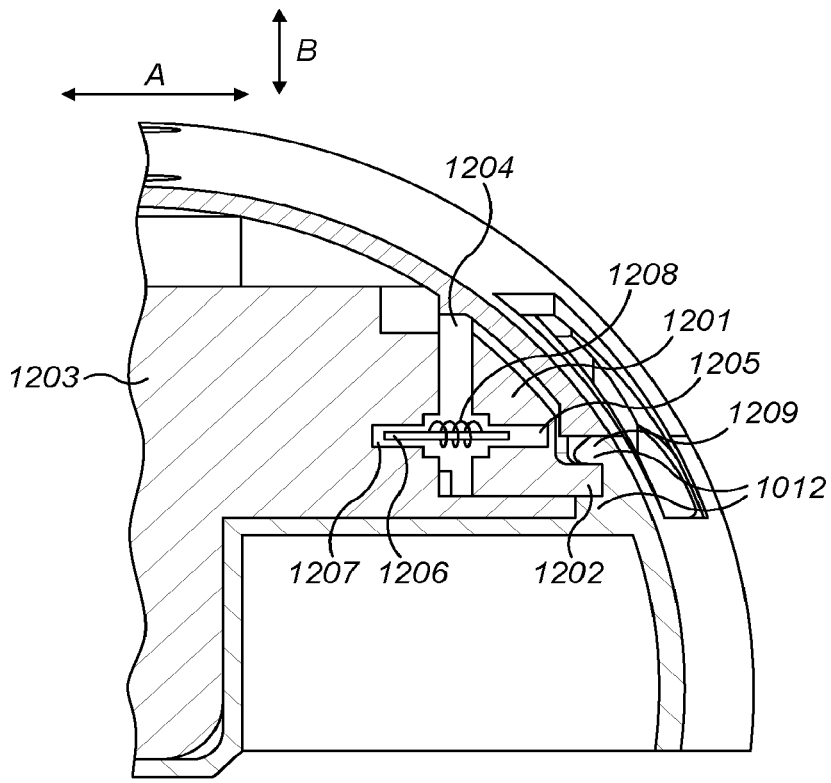
FIG. 12 illustrates a partial cross-section through FIG. 11.

FIG. 12 illustrates a partial cross-section through FIG. 11 in a direction transverse to the longitudinal axis of the instrument shaft 408, along the line HH. This figure illustrates the configuration of one engagement portion 1101. The engagement portion comprises a displaceable component 1201. Displaceable component 1201 comprises a plurality of nibs 1202, each of which is configured to engage a first fastener 1006 of the interface structure in the engaged configuration. Each nib 1202 is of a complementary shape to the first fastener 1006. In the example of FIG. 12, each nib has a plug shape thereby enabling it to engage into the socket formed by the protruding elements 1012 of the engagement structure. The displaceable component 1201 may comprise two nibs 1202, one of which engages first fastener 1006a, the other of which engages first fastener 1006b. The nibs 1202 are shaped so as to push the instrument interface down onto the engagement structure as the nibs engage the first fasteners.

Displaceable component 1201 is separated from internal body 1203 of the instrument by spacing 1204. Displaceable component 1201 is displaceable towards internal body 1203 through spacing 1204 in the direction A transverse to the longitudinal axis of the instrument shaft. Any suitable arrangement may be used to constrain displaceable component 1201 to movement only along direction A. In FIG. 12, displaceable component 1201 comprises a recess 1205 which houses a pin 1206. Recess 1205 and pin 1206 are parallel to the direction A. Pin 1206 extends into a corresponding recess 1207 in the internal body 1203. Pin 1206 is shorter than the total length of recesses 1205 and 1207 by at least the width of the spacing 1204 in the direction A. Pin 1206 is constrained to moving along direction A within recesses 1205 and 1207. Pin 1206 thereby constrains the displaceable component 1201 to sliding relative to internal body 1203 along the direction A only. Spring 1208 spans the spacing 1204 and is seated within recesses in the internal body 1203 and displaceable component 1201. Spring 1208 may be wound around pin 1206. Spring 1208 accommodates movement of the displaceable component 1201 towards the internal body 1203, but biases the displaceable component 1201 away from the internal body 1203. The pin and recess arrangement also causes the instrument and the interface structure to be aligned, since pin 1206 is only moveable into recess 1207, thereby only allowing the engagement portion 1101 to be actuated when recess 1205 and recess 1207 are aligned.

The engagement portion 1101 is moveable between a disengaged position in which the instrument can be lifted free from the interface structure, and an engaged position in which the instrument cannot be lifted free from the interface structure. FIG. 12 illustrates the engaged configuration in which the instrument is engaged in the interface structure 1000. Spring 1208 causes the internal body 1203 and the displaceable component 1201 to be separated by their maximum separation. At this maximum separation, nib 1202 of the instrument is engaged in protruding elements 1012. In other words, the instrument is docked in the interface structure 1000. At the other end of the displaceable range of the engagement portion 1101, spring 1208 is compressed, and displaceable component 1201 is pushed towards internal body 1203. This causes nib 1202 to disengage from protruding elements 1012. By applying pressure on the engagement portion(s) in the direction A towards the interior of the instrument, the instrument disengages from the interface structure 1000. The instrument is then lifted in the direction B away from the interface structure 1000 to remove the instrument from the robot arm. Suitably, in the disengaged position, the engagement portion 1101 sits inside the casework of the instrument, such that the casework forms a lip. This enables the user to more easily grip the instrument in the disengaged position. To engage the instrument with the interface structure 1000, pressure is applied on the engagement portion(s) in the direction A towards the interior of the instrument, and then the instrument is pushed in the direction B towards the interface structure. Once the instrument is aligned with the interface structure and in contact with the interface structure, the pressure on the engagement portion(s) is released. The force of the spring thereby pushes the nibs 1202 of the instrument into engagement with the protruding elements 1012.

The protrusion 1012 of each first fastener may be shaped with a lead-in feature so as to allow the nib 1202 to push over the protrusion 1012 into the engaged position without the user needing to push the engagement portion(s) in towards the interior of the instrument before applying the instrument to the interface structure. For example, rounded edge 1209 may enable the instrument to be push fitted onto the interface without manipulating the displaceable component 1201.

Figure 13:
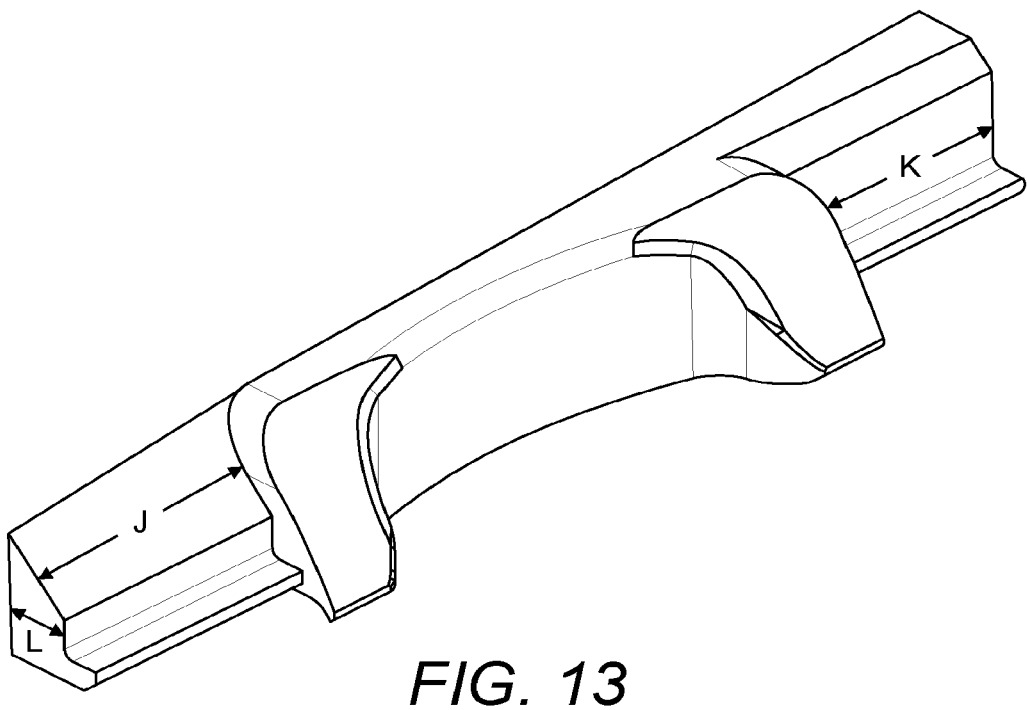
FIG. 13 illustrates the displaceable component 1201 of FIG. 12 in isolation.

A surgical instrument may attach to a surgical robot arm via the interface structure 1400 of FIG. 14 in the same manner as described with respect to the interface structure 1000 and FIGS. 11, 12 and 13.

Other arrangements may be used to facilitate movement of the instrument between a position in which the instrument is engaged in the first fasteners 1006, and the instrument is disengaged from the first fasteners 1006. For example, an engagement portion of the instrument may be rotatable about a longitudinal axis of a first fastener 1006. The engagement portion may rotate from an engaged position in which a nib of the engagement portion is engaged in the protrusions 1012 of the first fastener, to a disengaged position in which the nib is not engaged in the protrusions 1012 of the first fastener. Instead of being rotatable about the longitudinal axis of the first fastener, the engagement portion may be hinged about the longitudinal axis of the first fastener.

FIG. 13 illustrates the displaceable component 1201 of FIG. 12 in isolation. A first recess 1205, pin 1206 and spring 1208 mechanism may be located anywhere in the region marked J. A second recess 1205, pin 1206 and spring 1208 mechanism may be located anywhere in the region marked K. A plurality of recess, pin and spring mechanisms may be utilised in each region marked J and K. The springs of the plurality of recess, pin and spring mechanisms may be of different sizes.

The displaceable component 1201 may further comprise fasteners to fasten the displaceable component to the chassis of the instrument interface. The fasteners may, for example, be resilient lugs or clips. These may be located at the edges of the displaceable component in the region marked L on FIG. 13. The fasteners act to resist the springs 1208 and hence bias the displaceable component in the direction A (on FIG. 12) away from the interior of the instrument.

In addition to the engagement mechanism described above, a secondary locking mechanism may be implemented so as to prevent inadvertent removal of the instrument. For example, the secondary locking mechanism may secure the displaceable component 1201 to another part of the instrument, or to the interface structure or the robot arm. In this way, the displaceable component 1201 is prevented from being displaceable in the direction A towards the interior of the instrument. This secondary locking mechanism is disabled prior to removing the instrument from the robot arm. This secondary locking mechanism is disabled prior to attaching the instrument to the robot arm.

The exterior body of the instrument 1102 and the exterior body of the robot arm is shaped to be frustoconical when the instrument is docked to the robot arm.

In all the described examples, the engagement portion 901, 1101 is biased towards adopting the engaged position. The engagement portion may, for example, be spring-loaded so as to bias its position towards the engaged position.

The surgical instrument may comprise a wireless transmitter for sending wireless transmissions to the interface structure as described above. The surgical instrument may comprise a wireless transceiver for sending and receiving wireless communications as described above.

The interface structure may be packaged with the drape in a flat configuration. In the interface structure of FIG. 7, if the front and the rear wing portions are either separate from the base portion or hinged to the base portion, then the interface structure can adopt a substantially flat configuration. In the interface structure of FIG. 10, if the side flange portions and front wing portion are either separate from the base portion or hinged to the base portion, then the interface structure can adopt a substantially flat configuration. The interface structure is then folded into shape for use.

Suitably, the interface structure is fastened to the drive assembly as the robot arm is being shrouded in the sterile drape as part of the set-up procedure prior to the operation beginning. In the interface structure described with respect to FIG. 7 in which the rear wing portion is integrally formed with the base portion, the base portion and rear wing portion are attached to the robot arm first, by means of engaging the second and third fasteners in their respective recesses of the surgical robot arm. In this example, the front wing portion is either hinged to the base portion or is a separate piece. If the front wing portion is hinged to the base portion, then after the base portion and rear wing portion have engaged with the robot arm, the front wing portion is articulated down and fastened to the robot arm with the fourth fasteners. If the front wing portion is a separate piece, then this is separately fastened onto the robot arm and/or the base portion after the base portion and rear wing portion have engaged with the robot arm. In the interface structure described with respect to FIG. 10, the interface structure is push fitted onto the robot arm by applying force in the direction B towards the robot arm. In the interface structure described with respect to FIG. 14, the interface structure is push fitted onto the robot arm by applying force in the axial direction M (see FIG. 16). Once the interface structure has been pushed onto the arm, the drape is unravelled down the robot arm. Subsequently, the interface structure is secured to the robot arm using the third fasteners 1417.

In the examples described with respect to FIG. 7, an instrument is subsequently fastened to the interface structure 700. This is carried out by a user moving the engagement portion 901 in the direction D shown in FIG. 9. The direction D is parallel to the longitudinal axis of the instrument shaft towards the end effector. The direction D is parallel to the longitudinal axis of the interface structure away from the rear wing portion 702. The direction D is parallel to the longitudinal axis of the terminal link of the robot arm 508 away from the distal end 802 of the robot arm. For example, the user may slide the engagement portion 901 in the direction D. The user displaces the engagement portion 901 in the direction D until reaching the disengaged position. The user then brings the instrument into engagement with the interface structure by moving the instrument in a direction F, which is perpendicular to the longitudinal axis 408 of the instrument shaft towards the interface structure. The user may use the alignment features of 717 of the interface structure to aid alignment. By moving the instrument in the direction F, the instrument interface elements are more easily aligned with the drive assembly interface elements. The user then releases the engagement portion 901 thereby causing it to move in the direction E. Since the engagement portion 901 is biased towards adopting the engaged position, the engagement portion 901 moves in the direction E (see FIG. 9) until the nibs 904*a-d* of the engagement portion hit the walls 714 of the first fasteners 706*a-d*. This is the engaged position in which the nibs 904*a-d* of the engagement portion are engaged with the first fasteners 706*a-d* of the engagement structure.

At some point during the operation, the instrument is exchanged for another instrument. The instrument is detached from the interface structure 700 by the user moving the engagement portion 901 in the direction D until reaching the disengaged position. The user then lifts the instrument off the interface structure in a direction G which is perpendicular to the longitudinal axis 408 of the instrument shaft away from the interface structure. A different instrument can then be attached to the interface structure as previously described.

This method, and the corresponding ones described above with respect to the interface structures of FIG. 10 and FIG. 14, enable the instruments to be quickly and easily detached and attached to the robot arm during an operation without exposing the patient to a non-sterile environment. The instrument is removed by lifting it off the robot arm in a direction perpendicular to the shaft 402 of the instrument. Thus, there is no risk of pushing the instrument into the patient when detaching or attaching it.

The first fasteners depicted in the figures have the form of a socket for receiving a plug/nib from the instrument. The second and fourth fasteners depicted in the figures have the form of a clip for clipping into the recesses of the robot arm. The third fastener depicted in the figure has a latch arrangement for hooking over a ledge of the robot arm. However, the fasteners may take any suitable form, for example clips, clasps, buckles, latches, plugs, sockets, hooks, eyes, poppers, eyelets, buttons, Velcro, as long as the following criteria are satisfied:
 1) the interface structure remains attached to the robot arm when the instrument is detached.
 2) the interface structure, instrument and robot arm do not shift relative to each other along their longitudinal axes as articulation of the instrument is driven by the robot arm.

In the examples described with respect to FIG. 7, the interface structure comprises the base portion 701, the rear wing portion 702 and the front wing portion 703. Alternatively, the interface structure may be as described above but without the rear wing portion 702. Alternatively, the interface structure may be as described above but without the front wing portion 703. Alternatively, the interface structure may be as d escribed above but without the rear wing portion 702 and without the front wing portion 703.

The instrument could be used for non-surgical purposes. For example it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical instrument for use in robotic surgery, the surgical instrument comprising:
 a shaft;
 a surgical end effector at a distal end of the shaft; and
 an interfacing portion at a proximal end of the shaft for interfacing a surgical robot arm via an interface structure, the interfacing portion comprising:
  a body configured to engage a plurality of first fasteners of the interface structure; and
  an engagement portion comprising a plurality of nibs, the engagement portion being slidably displaceable relative to the body along the direction of the longitudinal axis of the instrument shaft and having a displaceable range between a disengaged position and an engaged position, wherein the disengaged position is at a first end of the displaceable range closest to the surgical end effector at which each nib is configured to disengage with a respective first fastener of the plurality of first fasteners of the interface structure, and wherein the engaged position is at a second end of the displaceable range farthest from the surgical end effector at which each nib is configured to engage with a respective first fastener of the plurality of first fasteners of the interface structure, wherein in the disengaged position the instrument can be lifted free from the interface structure and in the engaged position the instrument cannot be lifted free from the interface structure.

2. A surgical instrument as claimed in claim 1, wherein each nib has a plug shape that is configured to engage with a socket formed by a combination of the respective first fastener with which the respective nib is configured to engage and a base portion of the interface structure.

3. A surgical instrument as claimed in claim 1, wherein the engagement portion is spring loaded so as to bias its position towards the second end of the displaceable range farthest from the surgical end effector.

4. A surgical instrument as claimed in claim 1, wherein the body comprises at least two recesses, each recess configured to receive at least one first fastener of the plurality of first fasteners of the interface structure.

5. A surgical instrument as claimed in claim 1, wherein the surgical robot arm comprises a drive assembly having drive assembly interface elements and wherein the interfacing portion comprises instrument interface elements configured to engage with the drive assembly interface elements of the surgical robot arm.

6. A surgical instrument as claimed in claim 1, wherein the surgical robot arm comprises a drive assembly interface and wherein the interface structure is attached to a drape, the drape being configured to provide an interface between the drive assembly interface of the surgical robot arm and an instrument interface of the surgical instrument.

7. A surgical instrument as claimed in claim 1, wherein the surgical instrument comprises a sterile instrument interface and the surgical robot arm comprises a drive assembly having a drive assembly interface and wherein the interface structure prevents the drive assembly interface from directly touching the sterile instrument interface to maintain a sterile barrier between the drive assembly interface and the sterile instrument interface.

* * * * *